(12) United States Patent
Wu et al.

(10) Patent No.: US 8,188,314 B2
(45) Date of Patent: May 29, 2012

(54) BENZYLOXY ANILIDE DERIVATIVES USEFUL AS POTASSIUM CHANNEL MODULATORS

(75) Inventors: Jim Zhen Wu, Shanghai (CN); Jean-Michel Vernier, Laguna Niguel, CA (US); Huanming Chen, Irvine, CA (US); Jianlan Song, Cerritos, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 28 days.

(21) Appl. No.: 12/491,055

(22) Filed: Jun. 24, 2009

(65) Prior Publication Data
US 2009/0326059 A1    Dec. 31, 2009

Related U.S. Application Data

(60) Provisional application No. 61/075,307, filed on Jun. 24, 2008.

(51) Int. Cl.
*C07C 233/00*    (2006.01)
(52) U.S. Cl. .......... 564/220; 564/48; 564/123; 564/189; 514/546; 514/629; 560/167
(58) Field of Classification Search ........................ None
See application file for complete search history.

(56) References Cited

U.S. PATENT DOCUMENTS
6,762,320 B2 *  7/2004  Jolidon et al. ................ 564/157

FOREIGN PATENT DOCUMENTS
WO    WO 9849152 A1 *  11/1998
WO    WO 2008020607 A1 *  2/2008

OTHER PUBLICATIONS

S.R.Vippagunta, H.G.Brittain, D.J.W.Crant, Crystalline Solids, Advanced Drug Delivery Reviews, 2001, 48, 3-26.*
West, Anthony R., Solid State Chemistry and its Applications, Wiley, New York, 1988, pp. 358 & 365.*
Xue et al (Bioorganic & Medicinal Chemistry Letters, 2003, 13(24), 4293-4297).*

* cited by examiner

*Primary Examiner* — Sudhakar Katakam
(74) *Attorney, Agent, or Firm* — Jones Day

(57) ABSTRACT

The present invention relates to benzyloxyanilide derivatives having the following structural formula:

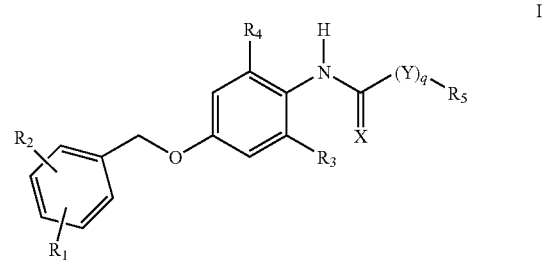

The compounds of the present invention are useful for the treatment and prevention of diseases and disorders which are affected by activation or modulation of potassium ion channels. One such condition is seizure disorders.

4 Claims, No Drawings

BENZYLOXY ANILIDE DERIVATIVES USEFUL AS POTASSIUM CHANNEL MODULATORS

This application claims the benefit of priority of U.S. provisional application Ser. No. 61/075,307, filed Jun. 24, 2008, the entire contents of which is incorporated herein by reference.

FIELD OF THE INVENTION

This invention provides benzyloxy anilide derivatives which activate or otherwise modulate voltage-gated potassium channels. The compounds are useful for the treatment and prevention of diseases and disorders which are affected by modulation of potassium ion channels. One such condition is seizure disorders.

BACKGROUND OF THE INVENTION

Epilepsy is a well-known neurological disease, found in about 3% of the population. Approximately 30% of patients with epilepsy do not respond to currently available therapies. Such unfortunate patients—who number hundreds of thousands of people world-wide—must contend with both uncontrolled seizures and the resulting narrowing of their options in such crucial areas of life as health insurance, employment, and driving.

Retigabine (N-[2-amino-4-(4-fluorobenzylamino)phenyl] carbamic acid, ethyl ester) (U.S. Pat. No. 5,384,330) has been found to be an effective treatment of seizure disorders and has also been found useful in treating pain. Retigabine has been found to be particularly potent in models for the drug-refractory types of epilepsy. Bialer, M. et al., *Epilepsy Research* 1999, 34, 1-41; Blackburn-Munro and Jensen, *Eur. J. Pharmacol.* 2003, 460, 109-116; Wickenden, A. D. et al., *Expert Opin. Ther. Patents,* 2004, 14(4).

"Benign familial neonatal convulsions," an inherited form of epilepsy, has been associated with mutations in the KCNQ2/3 channels. Biervert, C. et al., *Science* 1998, 27, 403-06; Singh, N. A., et al., *Nat. Genet.* 1998, 18, 25-29; Charlier, C. et al., *Nat. Genet.* 1998, 18, 53-55; Rogawski, *Trends in Neurosciences* 2000, 23, 393-398. Subsequent investigations have established that one important site of action of retigabine is the KCNQ2/3 channel. Wickenden, A. D. et al., *Mol. Pharmacol.* 2000, 58,591-600; Main, M. J. et al., *Mol. Pharmcol.* 2000, 58, 253-62. Retigabine has been shown to increase the conductance of the channels at the resting membrane potential, with a possible mechanism involving binding of the activation gate of the KCNQ 2/3 channel. Wuttke, T. V., et al., *Mol. Pharmacol.* 2005. Additionally, retigabine has been shown to increase neuronal M currents and to increase the channel open probability of KCNQ 2/3 channels. Delmas, P. and Brown, D. A. *Nat. Revs Neurosci.*, vol. 6, 2005, 850-62; Tatulian, L. and Brown, D. A., *J. Physiol., (*2003) 549, 57-63.

The seizure type that has been most resistant to therapy is the so-called "complex partial seizure." Retigabine is active in several seizure models, including, as indicated above, models for drug-refractory epilepsy. Because of retigabine's broad spectrum of activity and its unusual molecular mechanism, there is hope that retigabine will be effective in management of several seizure types, including the complex partial seizure, which have been resistant to treatment. Porter, R. J., Nohria, V., and Rundfeldt, C., *Neurotherapeutics,* 2007, vol. 4, 149-154.

The recognition of retigabine as a potassium channel opener has inspired a search among compounds with structural features in common with retigabine for other compounds which can affect the opening of, or otherwise modulate, potassium ion channels.

BRIEF DESCRIPTION OF THE INVENTION

The present invention provides a compound of formula I

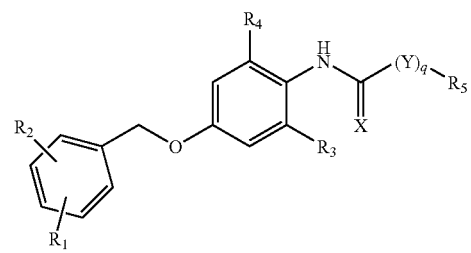

wherein $R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl; $NH_2$, NH—$C_1$-$C_6$ alkyl; $N(C_1$-$C_6$ alkyl, NHC(=O)$C_1$-$C_6$ alkyl, C(=O)N(CH_3)_2, C(=O)N(Et)_2, C(=O)NH_2, C(=O)NH-$C_1$-$C_6$ alkyl, $SO_2NH_2$, $NHSO_2$-$C_1$-$C_6$ alkyl; C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m C_3$-$C_6$ cycloalkyl, $C_3$-$C_6$ cycloalkenyl, $(CH_2)_m C_3$-$C_6$ cycloalkenyl, $C_2$-$C_6$ alkenyl, $C_2$-$C_6$ alkynyl, Ar, $(CH_2)_m$thienyl, $(CH_2)_m$furyl, $(CH_2)_m$imidazolyl, $(CH_2)_m$pyrazyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which are optionally substituted as described below; wherein m is zero, 1, or 2, Ar is a 5- to 10-member mono- or bicyclic aromatic group, optionally containing 1-4 ring heteroatoms selected independently from N, O, and S; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted as described below; $R_3$ and $R_4$ are, independently, H, CN, halogen, $CF_3$, $OCF_3$, $OC_1$-$C_3$ alkyl, or $C_1$-$C_6$ alkyl; X=O or S; Y is O or S; q=1 or zero; $R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$-$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, or $(CHR_6)_w CH_2$Ar, wherein w=zero, 1, 2, or 3, Ar is a 5- to 10-member mono- or bicyclic aromatic group, optionally containing 1-4 ring heteroatoms selected independently from N, O, and S; $R_6$ is H or $C_1$-$C_3$ alkyl; wherein all cycloalkyl and cycloalkenyl groups optionally contain one or two ring heteroatoms selected independently from N, O, and S; wherein all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, and Ar are optionally substituted with one or two substituents selected independently from $C_1$-$C_3$ alkyl, $OCF_3$, halogen, CN, OH, OMe, OEt, CN, $CH_2F$, and trifluoromethyl; and wherein, additionally, all cycloalkyl and heterocycloalkyl groups are optionally substituted with a carbonyl group, and halogen designates Cl, F, Br or I and the terms alkyl refers to branch or unbranched alkyl groups and pharmaceutically acceptable salts, solvates, and esters thereof. Such compounds are potassium channel activators or modulators.

Essentially all combinations of the several variables in formula I are embraced by this invention.

In another embodiment, this invention provides a composition comprising a pharmaceutically acceptable carrier or diluent and at least one of the following: a pharmaceutically effective amount of a compound of formula I, a pharmaceutically acceptable salt of a compound of formula I, a pharmaceutically acceptable solvate of a compound of formula I, and a pharmaceutically acceptable ester of a compound of formula I.

In yet another embodiment, this invention provides a pediatric pharmaceutical composition comprising a pharmaceutically acceptable carrier or diluent, a syrup for pediatric use, and at least one of the following: a pharmaceutically effective amount of a compound of formula I, a pharmaceutically acceptable salt of a compound of formula I, a pharmaceutically acceptable ester of a compound of formula I, and a pharmaceutically acceptable solvate of a compound of formula I.

In yet another embodiment, this invention provides a chewable tablet, suitable for pediatric pharmaceutical use, comprising a pharmaceutically acceptable carrier or diluent, and at least one of the following: a pharmaceutically effective amount of a compound of formula I, a pharmaceutically acceptable salt of a compound of formula I, a pharmaceutically acceptable solvate of a compound of formula I, and a pharmaceutically acceptable ester of a compound of formula I.

In yet another embodiment, this invention provides a method of preventing or treating a disease or disorder which is affected by activation voltage-gated potassium channels, comprising administering to a patient in need thereof a therapeutically effective amount of a compound of formula IA or a salt or ester or solvate thereof.

This invention includes all tautomers and salts of compounds of this invention. This invention also includes all compounds of this invention wherein one or more atoms are replaced by a radioactive isotope thereof.

This invention provides compounds of formula I above wherein the group NH—C(=X)—(Y)$_q$—R$_5$ is each of the following: NHC(=O)R$_5$, NHC(=O)OR$_5$, NHC(=S)R$_5$, NHC(=S)SR$_5$, NHC(=S)OR$_5$, and NHC(=O)SR$_5$.

Thus, in one embodiment, this invention provides a compound of formula I, wherein NH—C(=X)—(Y)$_q$—R$_5$ is NHC(=O)R$_5$.

In another embodiment, this invention provides a compound of formula I, wherein NH—C(=X)—(Y)$_q$—R$_5$ is NHC(=S)R$_5$.

In another embodiment, this invention provides a compound of formula I, wherein NH—C(=X)—(Y)$_q$—R$_5$ is NHC(=S)SR$_5$.

In another embodiment, this invention provides a compound of formula I, wherein NH—C(=X)—(Y)$_q$—R$_5$ is each NHC(=O)OR$_5$.

In another embodiment, this invention provides a compound of formula I, wherein NH—C(=X)—(Y)$_q$—R$_5$ is NHC(=S)OR$_5$.

In another embodiment, this invention provides a compound of formula I, wherein NH—C(=X)—(Y)$_q$—R$_5$ is NHC(=O)SR$_5$.

In another generic embodiment, this invention provides a compound of formula I, wherein q is zero and R$_5$ is C$_1$-C$_6$ alkyl, or (CHR$_6$)$_w$C$_3$-C$_6$ cycloalkyl.

In another embodiment, this invention provides a compound of formula I wherein R$_1$ is located as shown below:

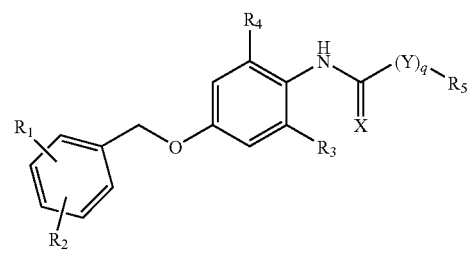

In another embodiment, R$_1$ is located as shown below:

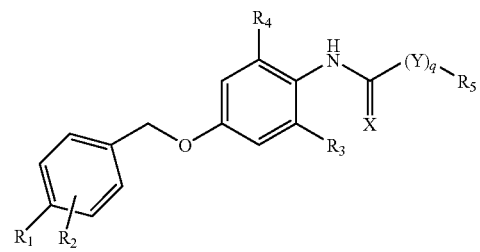

In another embodiment, R$_1$ is located as shown below

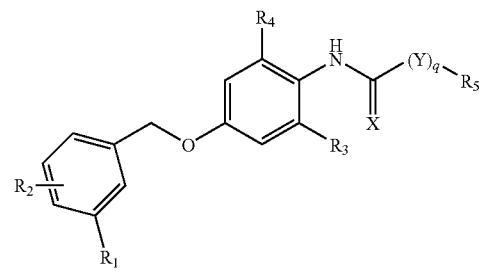

In another embodiment, this invention provides a compound of formula I, wherein R$_2$ is H.

In another embodiment, this invention provides a compound of formula I, wherein R$_2$ is halogen.

In another embodiment, this invention provides a compound of formula I, wherein R$_2$ is Cl or F.

In another embodiment, this invention provides a compound of formula I, wherein R$_2$ is trifluoromethyl.

In another embodiment, this invention provides a compound of formula I, wherein R$_3$ and R$_4$ are, independently, H, Cl, methyl, ethyl, trifluoromethyl, or methoxy.

In another embodiment, this invention provides a compound of formula I, wherein q is zero and R$_3$ and R$_4$ are Cl, ethyl, methoxy, or methyl.

In another embodiment, this invention provides a compound of formula I, wherein q is zero and R$_3$ and R$_4$ are both methyl.

In another embodiment, this invention provides a compound of formula I, wherein R$_3$ and R$_4$ are, independently, H, Cl, ethyl, methoxy, or methyl.

In another embodiment, this invention provides a compound of formula I, wherein R$_3$ and R$_4$ are, independently, H, Cl, ethyl, methoxy, or methyl.

In another embodiment, this invention provides a compound of formula I, wherein $R_3$ and $R_4$ are, independently, H, Cl, ethyl, or methyl.

In another embodiment, this invention provides a compound of formula I, wherein q is zero, and $R_5$ is $C_1$-$C_6$ alkyl, or $(CHR_6)_w C_3$-$C_6$ cycloalkyl.

In another embodiment, this invention provides a compound of formula I, wherein q is 1; Y is O; and $R_5$ is $C_1$-$C_6$ alkyl, or $(CHR_6)_w C_3$-$C_6$ cycloalkyl.

In another embodiment, this invention provides a compound of formula I, wherein q is 1; Y is S; and $R_5$ is $C_1$-$C_6$ alkyl, or $(CHR_6)_w C_3$-$C_6$ cycloalkyl.

In another embodiment, this invention provides a compound of formula I, wherein $R_2$ is H and $R_5$ is $C_1$-$C_6$ alkyl, or $(CHR_6)_w C_3$-$C_6$ cycloalkyl.

In another embodiment, this invention provides a compound of formula I, wherein $R_2$ is H and $R_5$ is Ar, $(CHR_6)_w$Ar, $CH_2(CHR_6)_w$Ar, or $(CHR_6)_w CH_2$Ar.

In another embodiment, this invention provides a compound of formula I, wherein $R_2$ is H and $R_5$ is $(CHR_6)_w C_5$-$C_6$ cycloalkenyl, $CH_2(CHR_6)_w C_5$-$C_6$ cycloalkenyl, $C_2$-$C_6$ alkynyl.

In another embodiment, this invention provides a compound of formula I, wherein $R_2$ is H and $R_5$ is $CR_6$=CH—$C_3$-$C_6$ cycloalkyl or CH=$CR_6$-$C_3$-$C_6$ cycloalkyl.

In another embodiment, this invention provides a compound of formula I, wherein $R_3$ and $R_4$ are H, Cl, ethyl, or methyl.

In another embodiment, this invention provides a compound of formula I, wherein $R_1$ is Cl or F; and $R_3$ and $R_4$ are H, Cl, ethyl, or methyl.

In another embodiment, this invention provides a compound of formula I, wherein $R_1$ is Cl or F; $R_3$ and $R_4$ are H, Cl, ethyl, or methyl; and $R_5$ is $C_1$-$C_6$ alkyl, or $(CHR_6)_w C_3$-$C_6$ cycloalkyl.

In another embodiment, this invention provides a compound of formula I, wherein $R_1$ is phenyl, optionally substituted.

In another embodiment, this invention provides a compound of formula I, wherein $R_1$ is phenyl, optionally substituted, and $R_5$ is $C_1$-$C_6$ alkyl, or $(CHR_6)_w C_3$-$C_6$ cycloalkyl.

In another embodiment, this invention provides a compound of formula I, wherein $R_1$ is NH—$C_1$-$C_6$ alkyl, N($C_1$-$C_6$ alkyl)-$C_1$-$C_6$ alkyl, C(=O)NH—$C_1$-$C_6$ alkyl, NH—C(=O) $C_1$-$C_6$ alkyl; and $R_5$ is $C_1$-$C_6$ $C_1$-$C_6$ alkyl, C(=O)—$C_1$-$C_6$ alkyl, C(=O)—O$C_1$-$C_6$ alkyl, or OC(=O)$C_1$-$C_6$ alkyl; and $R_5$ is $C_1$-$C_6$ alkyl, or $(CHR_6)_w C_3$-$C_6$ cycloalkyl.

In another embodiment, this invention provides a compound of formula I, wherein $R_1$ is NH—$C_1$-$C_6$ alkyl, N($C_1$-$C_6$ alkyl)-$C_1$-$C_6$ alkyl, C(=O)NH—$C_1$-$C_6$ alkyl, or NH—C(=O)$C_1$-$C_6$ alkyl.

In yet another embodiment, this invention provides a compound of formula I, wherein $R_1$ is C(=O)O$C_1$-$C_6$ alkyl, OC(=O)$C_1$-$C_6$ alkyl, or O$C_1$-$C_6$ alkyl.

In another specific embodiment, this invention provides a compound of formula I, wherein $R_1$ is H, methyl, methoxy, or halogen, and $R_2$ is methyl or ethyl.

In another embodiment, this invention provides a compound of formula I, wherein $R_1$ is H, methyl, methoxy, or halogen, and $R_2$ is phenyl.

In another embodiment, this invention provides a compound of formula I, wherein $R_1$ is H, methyl, methoxy, or halogen, and $R_2$ is F.

In another embodiment, this invention provides a compound of formula I, wherein $R_1$ is methoxy, methoxymethyl, ethoxymethyl, or methoxyethyl.

In another embodiment, this invention provides a compound of formula I, wherein $R_1$ is methoxy, methoxymethyl, ethoxymethyl, or methoxyethyl; $R_2$ is H, methyl, or halogen; and $R_3$ is methyl or Cl.

In another embodiment, this invention provides a compound of formula I, wherein $R_1$ is phenyl, optionally substituted, and $R_2$ is H, methyl, methoxy, or halogen.

In another embodiment, this invention provides a compound of formula I, wherein $R_1$ is $CF_3$ or $C_1$-$C_3$ alkyl, and $R_2$ is H, methyl, methoxy, or halogen.

In another embodiment, this invention provides a compound of formula I, wherein $R_1$ is methoxy, and $R_2$ is H, methyl, methoxy, or halogen.

In another embodiment, this invention provides a compound of formula I, wherein $R_1$ is 2-dimethylamino ethyl, and $R_2$ is H, methyl, methoxy, or halogen.

In another embodiment, this invention provides a compound of formula I, wherein q is zero, $R_2$ is H, methyl, methoxy, or halogen, $R_1$ is phenyl, optionally substituted; and $R_3$ and $R_4$ are H, Cl, ethyl, or methyl.

In another embodiment, this invention provides a compound of formula I, wherein q is zero, $R_2$ is H, methyl, methoxy, or halogen; $R_1$ is $CF_3$ or $C_1$-$C_3$ alkyl; and $R_3$ and $R_4$ are H, Cl, ethyl, or methyl.

In another embodiment, this invention provides a compound of formula I, wherein q is zero, $R_2$ is H, methyl, methoxy, or halogen; $R_1$ is F; and $R_3$ and $R_4$ are H, Cl, ethyl, or methyl.

In another embodiment, this invention provides a compound of formula I, wherein q is zero; $R_1$ is Br; $R_2$ is H, methyl, methoxy, or halogen; and $R_3$ and $R_4$ are H, Cl, ethyl, or methyl.

In another embodiment, the invention provides a compound of formula IA-1 below.

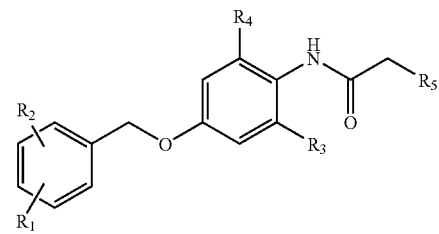

IA-1 wherein $R_1$ is selected from the group consisting of H, halogen, CN, $CH_2CN$, $CHF_2$, $CF_3$, $C_1$-$C_6$ alkyl, $OCH_3$, (C=O)$OCH_3$, O(C=O)$CH_3$, $OCF_3$, $(CH_2)_m C_3$-$C_6$ cycloalkyl, phenyl, and pyridyl; $R_2$ is selected from the group consisting of H, F, $OCH_3$, $CH_3$, and $CF_3$; $R_3$ and $R_4$, are independently, selected from the group consisting of H, F, Cl, $CF_3$, $OCF_3$, $OC_1$-$C_3$ alkyl, and $C_1$-$C_3$ alkyl; and $R_5$ is selected from the group consisting of $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, and $(CHR_6)_w CH_2$Ar, wherein w=0-3, Ar is selected from the group consisting of phenyl, furyl, pyrrolyl, oxazolyl, thiazolyl, thienyl, and pyridyl; and $R_6$ is $C_1$-$C_3$ alkyl; wherein all alkyl, cycloalkyl, aryl, and heteroaryl groups in $R_1$, $R_2$, $R_3$, $R_4$, $R_5$, and $R_6$, and Ar are optionally substituted with one or two substituents selected independently from $C_1$-$C_3$ alkyl, halogen, $OCH_3$, $OCH_2CH_3$, CN, and $CF_3$.

In another embodiment, this invention provides a compound of formula IA-2 below.

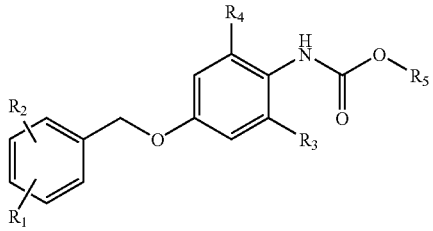

IA-2 wherein $R_1$ is selected from the group consisting of H, halogen, CN, $CH_2CN$, $CHF_2$, $CF_3$, $C_1$-$C_6$ alkyl, $OCH_3$, (C=O)$OCH_3$, $O(C=O)CH_3$, $OCF_3$, $(CH_2)_m C_3$-$C_6$ cycloalkyl, phenyl, and pyridyl; $R_2$ is selected from the group consisting of H, F, $OCH_3$, $CH_3$, and $CF_3$; $R_3$ and $R_4$, are independently, selected from the group consisting of H, F, Cl, $CF_3$, $OCF_3$, $OC_1$-$C_3$ alkyl, and $C_1$-$C_3$ alkyl; and $R_5$ is selected from the group consisting of $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, and $(CHR_6)_w CH_2$Ar, wherein w=0-3, Ar is selected from the group consisting of phenyl, furyl, pyrrolyl, oxazolyl, thiazolyl, thienyl, and pyridyl; and $R_6$ is $C_1$-$C_3$ alkyl; wherein all alkyl, cycloalkyl, aryl, and heteroaryl groups in $R_1$, $R_2$, $R_3$, $R_4$, $R_5$, and $R_6$, and Ar are optionally substituted with one or two substituents selected independently from $C_1$-$C_3$ alkyl, halogen, $OCH_3$, $OCH_2CH_3$, CN, and $CF_3$.

In still another embodiment, this invention provides a compound of formula IA-3 below.

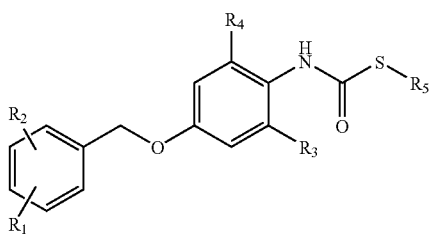

IA-3

In yet another embodiment, this invention provides a compound of formula IB-1 below.

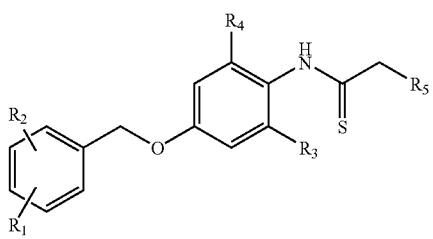

IB-1

In another specific embodiment, this invention provides a compound of formula IB-2 below.

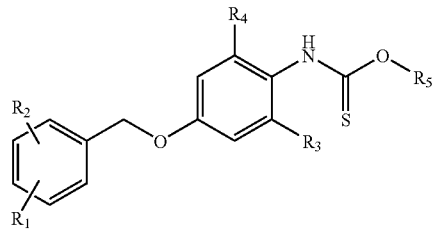

IB-2

In another specific embodiment, this invention provides a compound of formula IB-3 below.

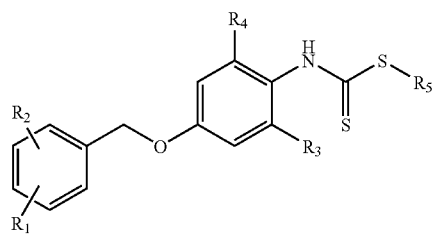

IB-3

In formulas IA-3, IB-1, IB-2 and IB-3, $R_1$, $R_2$, $R_3$, $R_4$ and $R_5$ are defined as in formula I.

In another more specific embodiment, this invention provides a compound of formula IA-1, formula IA-2, or formula IA-3, wherein $R_2$ is H, alkyl, or halogen; and $R_5$ is $C_1$-$C_6$ alkyl, $(CHR6)_w C_3$-$C_6$ cycloalkyl, $(CHR_6)_w CH_2 C_3$-$C_6$ cycloalkyl, or $CH_2(CHR6)_w C_3$-$C_6$ cycloalkyl.

In another specific embodiment, this invention provides a compound of formula IA-1, formula IA-2, or formula IA-3, wherein $R_1$ is $(CH_2)_m C_3$-$C_6$ cycloalkyl; $R_2$ is H, alkyl, or halogen; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another specific embodiment, this invention provides a compound of formula IA-1, formula IA-2, or formula IA-3, wherein $R_1$ is methoxy, methoxymethyl, or methoxyethyl; $R_2$ is H, alkyl, or halogen; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In yet another specific embodiment, this invention provides a compound of formula IA-1, wherein $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In yet another specific embodiment, this invention provides a compound of formula IA-2, wherein $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In yet another specific embodiment, this invention provides a compound of formula IA-1, wherein $R_5$ is Ar, $(CHR_6)_w$Ar, $CH_2(CHR_6)_w$Ar, or $(CHR_6)_w CH_2$Ar.

In yet another specific embodiment, this invention provides a compound of formula IA-2, wherein $R_5$ is Ar, $(CHR_6)_w$Ar, $CH_2(CHR_6)_w$Ar, or $(CHR_6)_w CH_2$Ar.

In yet another embodiment, this invention provides a compound of formula IA-3, wherein $R_5$ is Ar, $(CHR_6)_w$Ar, $CH_2(CHR_6)_w$Ar, or $(CHR_6)_w CH_2$Ar.

In yet another embodiment, this invention provides a compound of formula IA-1, wherein $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In yet another embodiment, this invention provides a compound of formula IA-2, wherein $R_5$ is $CR_6=CH-C_3-C_6$ cycloalkyl, $CH=CR_6-C_3-C_6$ cycloalkyl, $(CHR_6)_w C_5-C_6$ cycloalkenyl, $CH_2(CHR_6)_w C_5-C_6$ cycloalkenyl, $C_2-C_6$ alkenyl, or $C_2-C_6$ alkynyl.

In yet another embodiment, this invention provides a compound of formula IA-1, wherein $R_2$ is H; $R_3$ is methyl; and $R_5$ is $C_1-C_6$ alkyl, $(CHR_6)_w C_3-C_6$ cycloalkyl, $(CHR_6)_w CH_2 C_3-C_6$ cycloalkyl, or $CH_2(CHR_6)_w C_3-C_6$ cycloalkyl.

In yet another embodiment, this invention provides a compound of formula IA-2, wherein $R_2$ is H; $R_3$ is methyl; and $R_5$ is $C_1-C_6$ alkyl, $(CHR_6)_w C_3-C_6$ cycloalkyl, $(CHR_6)_w CH_2 C_3-C_6$ cycloalkyl, or $CH_2(CHR_6)_w C_3-C_6$ cycloalkyl.

In yet another embodiment, this invention provides a compound of formula IA-3, wherein $R_2$ is H; $R_3$ is methyl; and $R_5$ is $C_1-C_6$ alkyl, $(CHR_6)_w C_3-C_6$ cycloalkyl, $(CHR_6)_w CH_2 C_3-C_6$ cycloalkyl, or $CH_2(CHR_6)_w C_3-C_6$ cycloalkyl.

In another embodiment, this invention provides a compound of formula IA-1, wherein $R_1$ is H, F, Cl, Br, methoxy, methoxymethyl, ethoxymethyl, methoxyethyl, or trifluoromethyl; $R_3$ is methyl; and $R_5$ is $C_4-C_6$ alkyl, $(CHR_6)_w CH_2 C_5-C_6$ cycloalkyl, or $CH_2(CHR_6)_w C_5-C_6$ cycloalkyl.

In another embodiment, this invention provides a compound of formula IA-2, wherein $R_1$ is H, F, Cl, Br, methoxy, methoxymethyl, ethoxymethyl, methoxyethyl, or trifluoromethyl; $R_3$ is methyl; and $R_5$ is $C_4-C_6$ alkyl, $(CHR_6)_w CH_2 C_5-C_6$ cycloalkyl, or $CH_2(CHR_6)_w C_5-C_6$ cycloalkyl.

In another embodiment, this invention provides a compound of formula IA-1, wherein $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, methoxymethyl, ethoxymethyl, methoxyethyl, or trifluoromethyl.

In another embodiment, this invention provides a compound of formula IA-2, wherein $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl Br, methoxy, methoxymethyl, ethoxymethyl, methoxyethyl, or trifluoromethyl.

In another embodiment, this invention provides a compound of formula IA-1, wherein $R_1$ is H, F, Cl, Br, methoxy, methoxymethyl, ethoxymethyl, methoxyethyl, or trifluoromethyl; $R_2$ is H, methyl, or F; $R_3$ is methyl; $R_4$ is methyl or Cl; and $R_5$ is $C_4-C_6$ alkyl, $(CHR_6)_w C_5-C_6$ cycloalkyl, or $CH_2(CHR_6)_w C_5-C_6$ cycloalkyl.

In another embodiment, this invention provides a compound of formula IA-2, wherein $R_1$ is H, F, Cl, Br, methoxy, methoxymethyl, ethoxymethyl, methoxyethyl, or trifluoromethyl; $R_2$ is H, methyl, or F; $R_3$ is methyl; R4 is methyl or Cl; and $R_5$ is $C_4-C_6$ alkyl, $(CHR_6)_w C_5-C_6$ cycloalkyl, or $CH_2(CHR_6)_w C_5-C_6$ cycloalkyl.

In another embodiment, this invention provides a compound of formula IA-3, wherein $R_1$ is H, F, Cl, Br, methoxy, methoxymethyl, ethoxymethyl, methoxyethyl, or trifluoromethyl; $R_2$ is H, methyl, or F; $R_3$ is methyl; $R_4$ is methyl or Cl; and $R_5$ is $C_4-C_6$ alkyl, $(CHR_6)_w C_5-C_6$ cycloalkyl, or $CH_2(CHR_6)_w C_5-C_6$ cycloalkyl.

In another embodiment, this invention provides a compound of formula IA-1, wherein $R_1$ is $(CH_2)_m C_3-C_6$ cycloalkyl, $C_3-C_6$ cycloalkenyl, or $(CH_2)_m C_3-C_6$ cycloalkenyl; and $R_3$ is methyl or Cl.

In another embodiment, this invention provides a compound of formula IA-1, wherein $R_1$ is $(CH_2)_m C_3-C_6$ cycloalkyl, $C_3-C_6$ cycloalkenyl, or $(CH_2)_m C_3-C_6$ cycloalkenyl.

In another embodiment, this invention provides a compound of formula IA-1, wherein $R_1$ is methoxy, methoxymethyl, ethoxymethyl; or methoxyethyl; $R_2$ is H or F; $R_3$ is methyl; $R_4$ is methyl or Cl; and $R_5$ is $(CHR_6)_w C_5-C_6$ cycloalkenyl or $(CHR_6)_w Ar$.

In another embodiment, this invention provides a compound of formula IA-1, wherein $R_1$ is phenyl, optionally substituted.

In another embodiment, this invention provides a compound of formula IA-1, wherein $R_1$ is methyl, halomethyl, ethyl, or haloethyl.

In another embodiment, this invention provides a compound of formula IA-1, wherein $R_1$ is $C_1-C_4$ alkyl.

In another embodiment, this invention provides a compound of formula IA-1, wherein $R_1$ is methyl or ethyl.

In another embodiment, this invention provides a compound of formula IA-1, wherein $R_2$ is fluoro, $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-2, wherein $R_2$ is 4-fluoro, $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-1, wherein $R_1$ is $(CH_2)_m$imidazolyl, $(CH_2)_m$pyrazyl, $(CH_2)_m$ furyl, $(CH_2)_m$ thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl; and $R_2$ is H.

In another embodiment, this invention provides a compound of formula IA-2, wherein $R_1$ is $(CH_2)_m$imidazolyl, $(CH_2)_m$pyrazyl, $(CH_2)_m$ furyl, $(CH_2)_m$ thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl; $R_2$ is H and $R_5$ is pyridyl or phenyl, optionally substituted.

In another embodiment, this invention provides a compound of formula IA-2, wherein $R_2$ is $CF_3$ or $C_1-C_3$ alkyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-2, wherein $R_3$ and $R_4$ are methyl or trifluoromethyl; $R_5$ is $C_4-C_6$ alkyl, $(CHR6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-2, wherein $R_2$ is methoxy or ethoxy; and $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-2, wherein $R_2$ is phenyl, optionally substituted; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-1, wherein $R_1$ is $(CH_2)_m$imidazolyl, $(CH_2)_m$pyrazyl, $(CH_2)_m$ furyl, $(CH_2)_m$ thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl; $R_2$ is H; and $R_5$ is pyridyl or phenyl, optionally substituted.

In another embodiment, this invention provides a compound of formula IA-1, wherein $R_2$ is $CF_3$ or $C_1-C_3$ alkyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another embodiment, this invention provides a compound of formula IA-1, wherein $R_3$ and $R_4$ are methyl or trifluoromethyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein $R_2$ is methoxy or ethoxy; and $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein $R_2$ is phenyl, optionally substituted; $R_5$ is $C_4$-$C_6$ alkyl, $(CHR_6)_w C_5$-$C_6$ cycloalkyl, or $CH_2(CHR_6)_w C_5 C_6$ $C_6$ cycloalkyl; and $R_1$ is H, F, Cl, Br, methoxy, or trifluoromethyl.

In another embodiment, this invention provides a compound of formula IA-1, wherein R' is 4-phenyl, optionally substituted; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein R' is $CF_3$ or $C_1$-$C_3$ alkyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein R' is 4-methyl or 4-ethyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein R' is methoxy or ethoxy, $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein $R_1$ is H, F, Cl, Br, methoxy, or trifluoromethyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein $R_2$ is H, F, or methyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-2, wherein R' is H.

In another embodiment, this invention provides a compound of formula IA-2, wherein R' is halogen.

In another embodiment, this invention provides a compound of formula IA-2, wherein R' is F.

In another embodiment, this invention provides a compound of formula IA-2, wherein R' is methyl or ethyl.

In another embodiment, this invention provides a compound of formula IA-2, wherein R' is methyl or ethyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ and $R_1$ is H, F, Cl, Br, methoxy, or trifluoromethyl.

In another embodiment, this invention provides a compound of formula IA-2, wherein R' is halogen; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-2, wherein R' is H; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-2, wherein R' is 1-phenyl, optionally substituted.

In another embodiment, this invention provides a compound of formula IA-2, wherein R' is 4-phenyl, optionally substituted.

In another embodiment, this invention provides a compound of formula IA-2, wherein R' is $CF_3$ or $C_1$-$C_3$ alkyl.

In another embodiment, this invention provides a compound of formula IA-3, wherein R' is H; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-3, wherein R' is F; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-3, wherein R' is 1-phenyl, optionally substituted; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-3, wherein R' is 4-phenyl, optionally substituted; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-3, wherein $R_2$ is $CF_3$ or $C_1$-$C_3$ alkyl; $R_5$ is $C_4$-$C_6$ alkyl, $(CHR_6)_w C_5$-$C_6$ cycloalkyl, or $CH_2(CHR_6)_w C_5$-$C_6$ cycloalkyl; and $R_1$ is H, F, Cl, Br, methoxy, or trifluoromethyl.

In another embodiment, this invention provides a compound of formula IA-1, wherein $R_1$ and $R_2$, are, independently, H, CN, F, Cl, Br, $CH_2CN$, $OCH_3$, $CH_2OCH_3$, $CH_2CH_2OCH_3$, $CH_2OCH_2CH_3$; $CH_2F$, $CHF_2$, $CF_3$, $CF_2CF_3$, or $C_1$-$C_6$ alkyl and $R_5$ is $C_1$-$C_6$ alkyl or $CH_2(CHR_6)_w C_3$-$C_6$ cycloalkyl, wherein w=0, 1, or 2.

In another embodiment, this invention provides a compound of formula IA-1, $R_1$ is H, CN, F, Cl, Br, $CH_2CN$, $OCH_3$, $CH_2OCH_3$, $CH_2CH_2OCH_3$, $CH_2OCH_2CH_3$, $CH_2F$, $CHF_2$, $CF_3$, $CF_2CF_3$, or $C_1$-$C_6$ alkyl; $R_2$ is H, F, Cl, or methyl; $R_3$ is methyl or chloro; and $R_5$ is $C_1$-$C_6$ alkyl or $CH_2(CHR_6)_w C_3$-$C_6$ cycloalkyl, wherein $R_6$ is H or methyl and w=1 or 2.

In another embodiment, this invention provides a compound of formula IA, wherein $R_5$ is Ar, $(CHR_6)_w Ar$, $CH_2(CHR_6)_w Ar$, or $(CHR_6)_w CH_2 Ar$.

In another embodiment, this invention provides a compound of formula IA-2, wherein $R_5$ is Ar, $(CHR_6)_w Ar$, $CH_2(CHR_6)_w Ar$, or $(CHR_6)_w CH_2 Ar_1$.

In another embodiment, this invention provides a compound of formula IA-3, wherein $R_5$ is Ar, $(CHR_6)_w Ar$, $CH_2(CHR_6)_w Ar$, or $(CHR_6)_w CH_2 Ar$.

In another embodiment, this invention provides a compound of formula I, wherein $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another embodiment, this invention provides a compound of formula IA-1, wherein $R_5$ is $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In another embodiment, this invention provides a compound of formula I, wherein $R_5$ is haloalkyl.

In another embodiment, this invention provides a compound of formula IA-1, wherein $R_5$ is haloalkyl.

In another embodiment, this invention provides a compound of formula IA-2, wherein $R_5$ is haloalkyl.

In another embodiment, this invention provides a compound of formula IA-3, wherein $R_5$ is haloalkyl.

In another embodiment, this invention provides a compound of formula IB-1, wherein $R_5$ is haloalkyl.

In another embodiment, this invention provides a compound of formula IB-2, wherein $R_5$ is haloalkyl.

In another embodiment, this invention provides a compound of formula IB-3, wherein $R_5$ is haloalkyl.

In another embodiment, this invention provides a compound of formula I, wherein $R_5$ is methoxy alkyl.

In another embodiment, this invention provides a compound of formula I, wherein $R_5$ is cyano alkyl.

In another embodiment, the invention provides a compound of formula I, wherein $R_5$ is $CH_2$-cycloalkyl or $CH_2CH_2$-cycloalkyl.

In another embodiment, the invention provides a compound of formula IA-1, wherein $R_5$ is $CH_2$-cycloalkyl or $CH_2CH_2$-cycloalkyl.

In another embodiment, the invention provides a compound of formula IA-2, wherein $R_5$ is $CH_2$-cycloalkyl or $CH_2CH_2$-cycloalkyl.

In another embodiment, the invention provides a compound of formula IA-3, wherein $R_5$ is $CH_2$-cycloalkyl or $CH_2CH_2$-cycloalkyl.

In another embodiment, the invention provides a compound of formula IB-1, wherein $R_5$ is $CH_2$-cycloalkyl or $CH_2CH_2$-cycloalkyl.

In another embodiment, the invention provides a compound of formula IB-2, wherein $R_5$ is $CH_2$-cycloalkyl or $CH_2CH_2$-cycloalkyl.

In another embodiment, the invention provides a compound of formula IB-3, wherein $R_5$ is $CH_2$-cycloalkyl or $CH_2CH_2$-cycloalkyl.

In another embodiment, the invention provides a compound of formula IA-1, wherein $R_5$ is $CH_2$—$C_5$-$C_6$ cycloalkyl or $CH_2CH_2$—$C_5$-$C_6$ cycloalkyl.

In another embodiment, the invention provides a compound of formula IA-2, wherein $R_5$ is $CH_2$—$C_5$-$C_6$ cycloalkyl or $CH_2CH_2$—$C_5$-$C_6$ cycloalkyl.

In another embodiment, the invention provides a compound of formula IA-3, wherein $R_5$ is $CH_2$—$C_5$-$C_6$ cycloalkyl or $CH_2CH_2$—$C_5$-$C_6$ cycloalkyl.

In another embodiment, the invention provides a compound of formula IB-1, wherein $R_5$ is $CH_2$—$C_5$-$C_6$ cycloalkyl or $CH_2CH_2$—$C_5$-$C_6$ cycloalkyl.

In another embodiment, the invention provides a compound of formula IB-2, wherein $R_5$ is $CH_2$—$C_5$-$C_6$ cycloalkyl or $CH_2CH_2$—$C_5$-$C_6$ cycloalkyl.

In another embodiment, the invention provides a compound of formula IB-3, wherein $R_5$ is $CH_2$—$C_5$-$C_6$ cycloalkyl or $CH_2CH_2$—$C_5$-$C_6$ cycloalkyl.

In another embodiment, the invention provides a compound of formula IA-1, wherein $R_5$ is $C_5$-$C_6$ alkyl or $CH_2C_5$-$C_6$ alkyl.

In another embodiment, the invention provides a compound of formula IA-2, wherein $R_5$ is $C_5$-$C_6$ alkyl or $CH_2C_5$-$C_6$ alkyl.

In another embodiment, the invention provides a compound of formula IA-3, wherein $R_5$ is $C_5$-$C_6$ alkyl or $CH_2C_5$-$C_6$ alkyl.

In another embodiment, the invention provides a compound of formula IB-1, wherein $R_5$ is $C_5$-$C_6$ alkyl or $CH_2C_5$-$C_6$ alkyl.

In another embodiment, the invention provides a compound of formula IB-2, wherein $R_5$ is $C_5$-$C_6$ alkyl or $CH_2C_5$-$C_6$ alkyl.

In another embodiment, the invention provides a compound of formula IB-3, wherein $R_5$ is $C_5$-$C_6$ alkyl or $CH_2C_5$-$C_6$ alkyl.

In another embodiment, this invention provides a compound of formula IA-1, wherein $R_3$ and $R_4$ are chloro, methoxy, or methyl and $R_5$ is $CH_2$-cycloalkyl.

In another embodiment, this invention provides a compound of formula IA-1, wherein $R_3$ and $R_4$ are chloro, methoxy, or methyl and $R_5$ is haloalkyl, hydroxyalkyl, or methoxyalkyl.

In another embodiment, this invention provides a compound of formula IA-1, wherein $R_3$ and $R_4$ are methyl and $R_5$ is $C_5$-$C_6$ alkyl or methoxy alkyl.

In another embodiment, this invention provides a compound of formula IA-2, wherein $R_3$ and $R_4$ are methyl and $R_5$ is $C_5$-$C_6$ alkyl or chloroalkyl.

In another embodiment, this invention provides a compound of formula IA-2, wherein $R_3$ and $R_4$ are trifluoromethyl and $R_5$ is methoxyalkyl.

In another embodiment, this invention provides a compound of formula IA-1, wherein $R_3$ and $R_4$ are both methyl and $R_5$ is 2-(2-halo cyclopentyl)ethyl.

In another embodiment, this invention provides a compound of formula IA-1, wherein $R_3$ and $R_4$ are both methyl and $R_5$ is 2-(2-furyl)ethyl.

In another embodiment, this invention provides a compound of formula IA-1, wherein $R_3$ and $R_4$ are both methyl and $R_5$ is 2-(2-tetrahydrofuryl)ethyl.

In another embodiment, this invention provides a compound of formula IA-1, wherein $R_3$ and $R_4$ are both methyl and $R_5$ is 2-phenyl ethyl.

In another embodiment, this invention provides a compound of formula IA-1, wherein $R_3$ and $R_4$ are both methyl and $R_5$ is 3-phenyl propyl.

In another embodiment, this invention provides a compound of formula IA-1, wherein $R_3$ and $R_4$ are both methyl and $R_5$ is 2-phenyl propyl.

In another embodiment, this invention provides a compound of formula IA-1, wherein $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; and $R_1$ is halogen.

In another embodiment, this invention provides a compound of formula IA-1, wherein $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; $R_2$ is H or halogen; and $R_1$ is halogen.

In another embodiment, this invention provides a compound of formula IA-2, wherein $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; $R_2$ is H or halogen; and $R_1$ is halogen.

In another embodiment, this invention provides a compound of formula IA-3, wherein $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; $R_2$ is H or halogen; and $R_1$ is halogen.

In another embodiment, this invention provides a compound of formula IA-2, wherein $R_5$ is $C_1$-$C_6$ alkyl or $CH_2(CHR6)_wC_3$-$C_6$ cycloalkyl; $R_2$ is hydrogen; and $R_1$ is halogen.

In another embodiment, this invention provides a compound of formula IA-3, wherein $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; $R_2$ is hydrogen; and $R_1$ is halogen.

In another embodiment, this invention provides a compound of formula I, wherein $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA, wherein $R_5$ is Ar, $(CHR_6)_wAr$, $CH_2(CHR_6)_wAr$, or $(CHR_6)_wCH_2Ar_1$.

In another embodiment, this invention provides a compound of formula IA-3, wherein $R_1$ is haloalkyl; $R_2$ is H or F; $R_3$ and $R_4$ are Cl, methoxy, or methyl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another embodiment, this invention provides a compound of formula IA, wherein $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$—$C_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another embodiment, this invention provides a compound of formula IA-1, wherein $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$—C3-$C_6$ cycloalkyl, $CR_6$=CH—$C_3$-$C_6$ cycloalkyl, CH=$CR_6$—C3-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another embodiment, this invention provides a compound of formula IA-3, wherein $R_1$ is $C_1$-$C_3$ alkyl, halogen, or haloalkyl; $R_2$ is H or F; $R_3$ and R4 are H, methyl, or Cl; and $R_5$ is $CH_2CR_6$—$C_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another embodiment, this invention provides a compound of formula IA-1, wherein $R_1$ is $C_1$-$C_3$ alkyl, halogen, or haloalkyl; $R_2$ is H or F; $R_3$ and R4 are H, methyl, or Cl; and $R_5$ is $CH_2CR_6$—$C_3$-$C_6$ cycloalkyl, or $C_2$-$C_6$ alkyl.

In another embodiment, this invention provides a compound of formula IA-3, wherein $R_1$ is $C_1$-$C_3$ alkyl, halogen, or haloalkyl; $R_2$ is H or F; $R_3$ and R4 are H, methyl, or Cl; and $R_5$ is $CH_2CR_6$—$C_3$-$C_6$ cycloalkyl, $(CHR_6)_wC_5$-$C_6$ cycloalkenyl, $CH_2(CHR_6)_wC_5$-$C_6$ alkenyl, or $C_2$-$C_6$ alkynyl.

In another embodiment, this invention provides a compound of formula IA-3, wherein $R_1$ is halogen or haloalkyl; $R_2$ is H or F; and $R_5$ is $CR_6$=CH—$C_3$-$C_6$ cycloalkyl, CH=$CR_6$-$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA-3, wherein $R_1$ is halogen or haloalkyl; $R_2$ is H or F; and $R_5$ is $CR_6$=CH—$C_3$-$C_6$ cycloalkyl, CH=$CR_6$-$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA-3, wherein $R_1$ is halogen or haloalkyl; $R_2$ is H or F; $R_3$ and R4 are Cl, methoxy, or methyl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another embodiment, this invention provides a compound of formula IA-3, wherein $R_1$ is halogen or haloalkyl; $R_2$ is H or F; and $R_5$ is $CR_6$=CH-C3-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA-3, wherein $R_1$ is methyl, fluoro, or fluoroalkyl; $R_2$ is H or F; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another embodiment, this invention provides a compound of formula IA-3, wherein $R_1$ is Cl, F, or $CF_3$; $R_2$ is H or F; R' is H or $CH_3$; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl.

In another embodiment, this invention provides a compound of formula IA-3, wherein $R_1$ is Cl, F, or $CF_3$; $R_2$ is H or F; R' is H or $CH_3$; and $R_5$ is Ar, $(CHR_6)_wAr$, $CH_2(CHR_6)_wAr$, or $(CHR_6)_wCH_2Ar$.

In another embodiment, this invention provides a compound of formula IA-1, wherein $R_3$ and $R_4$ are H, methyl, or Cl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another embodiment, this invention provides a compound of formula IA-1, wherein $R_3$ and $R_4$ are H, methyl, or Cl; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA-1, wherein $R_3$ and $R_4$ are H, methyl, or Cl; and wherein $R_1$ and $R_2$, on adjacent carbons, form a six-membered ring.

In another embodiment, this invention provides a compound of formula IA-1, wherein $R_3$ and $R_4$ are H, methyl, or Cl; wherein $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and wherein $R_1$ and $R_2$, are on adjacent carbons, and are both other than H.

In another embodiment, this invention provides a compound of formula IA-1, wherein $R_3$ and $R_4$ are H, methyl, or Cl; wherein $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and wherein $R_1$ and $R_2$, on adjacent carbons, are both halogen.

In another embodiment, this invention provides a compound of formula IA-1, wherein $R_3$ and $R_4$ are H, methyl, or Cl; wherein $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and wherein $R_1$ and $R_2$, on adjacent carbons, are both fluorine.

In an embodiment, this invention provides a compound of formula IA-1, wherein R' is F, methyl, or H; $R_3$ and $R_4$ are H, methyl, or Cl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another embodiment, this invention provides a compound of formula IA-1, wherein R' is F, methyl, or H; $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another embodiment, this invention provides a compound of formula IA-1, wherein R' is halogen and $R_5$ is Ar, $(CHR6)_wAr$, $CH_2(CHR_6)_wAr$, or $(CHR_6)_wCH_2Ar_1$.

In another embodiment, this invention provides a compound of formula IA-1, wherein $R_1$ and $R_2$ are on adjacent carbon atoms and are both other than H.

In an embodiment, this invention provides a compound of formula IA-1, wherein $R_1$ and $R_2$, on adjacent carbon atoms are, independently trifluoromethyl or halogen; and wherein R$_5$ is C$_1$-C$_6$ alkyl, (CHR$_6$)$_w$C$_3$-C$_6$ cycloalkyl, (CHR$_6$)$_w$CH$_2$C$_3$-C$_6$ cycloalkyl, or CH$_2$(CHR$_6$)$_w$C$_3$-C$_6$ cycloalkyl.

In another embodiment, this invention provides a compound of formula IA-1, wherein R$_5$ is (CHR$_6$)$_w$C$_5$-C$_6$ cycloalkenyl, CH$_2$(CHR$_6$)$_w$C$_5$-C$_6$ cycloalkenyl, C$_2$-C$_6$ alkenyl, or C$_2$-C$_6$ alkynyl.

In another embodiment, this invention provides a compound of formula IA-1, wherein R$_1$ is halogen and R$_2$ is H, or R$_1$ and R$_2$, on adjacent carbon atoms are, independently trifluoromethyl or halogen; and wherein R$_5$ is CR$_6$=CH—C$_3$-C$_6$ cycloalkyl, CH=CR$_6$—C$_3$-C$_6$ cycloalkyl, (CHR$_6$)$_w$C$_5$-C$_6$ cycloalkenyl, CH$_2$(CHR$_6$)$_w$C$_5$-C$_6$ cycloalkenyl, C$_2$-C$_6$ alkenyl, or C$_2$-C$_6$ alkynyl.

In another embodiment, this invention provides a compound of formula IA-1, wherein R$_5$ is Ar, (CHR$_6$)$_w$Ar, CH$_2$(CHR$_6$)$_w$Ar, or (CHR$_6$)$_w$CH$_2$Ar$_1$.

In another embodiment, this invention provides a compound of formula IA-1, wherein R$_1$ is halogen or trifluoromethyl and R$_2$ is H, or R$_1$ and R$_2$, on adjacent carbon atoms are, independently trifluoromethyl or halogen; and wherein R$_5$ is Ar, (CHR$_6$)$_w$Ar, CH$_2$(CHR$_6$)$_w$Ar, or (CHR$_6$)$_w$CH$_2$Ar.

In another embodiment, this invention provides a compound of formula IA, wherein X is S, q=1, Y is O, and R$_5$ is C$_1$-C$_6$ alkyl, (CHR6)$_w$C$_3$-C$_6$ cycloalkyl, (CHR6)$_w$CH$_2$C$_3$-C$_6$ cycloalkyl, or CH$_2$(CHR6)$_w$C$_3$-C$_6$ cycloalkyl.

In another embodiment, this invention provides a compound of formula IA, wherein X is S, q=1, Y is O, and R$_5$ is CR$_6$=CH—C$_3$-C$_6$ cycloalkyl, CH=CR$_6$—C$_3$-C$_6$ cycloalkyl, (CHR6)$_w$C$_5$-C$_6$ cycloalkenyl, CH$_2$(CHR6)$_w$C$_5$-C$_6$ cycloalkenyl, C$_2$-C$_6$ alkenyl, or C$_2$-C$_6$ alkynyl.

In another embodiment, this invention provides a compound of formula IA, wherein X is S, q=1, Y is O, and R$_5$ is Ar, (CHR6)$_w$Ar, CH$_2$(CHR6)$_w$Ar, or (CHR6)$_w$CH$_2$Ar.

In another embodiment, this invention provides a compound of formula IA, wherein X is S, q=zero, and R$_5$ is C$_1$-C$_6$ alkyl, (CHR6)$_w$C$_3$-C$_6$ cycloalkyl, (CHR6)$_w$CH$_2$C$_3$-C$_6$ cycloalkyl, or CH$_2$(CHR6)$_w$C$_3$-C$_6$ cycloalkyl.

In another embodiment, this invention provides a compound of formula IA, wherein X is S, q=zero, and R$_5$ is CR$_6$=CH—C$_3$-C$_6$ cycloalkyl, CH=CR$_6$—C$_3$-C$_6$ cycloalkyl, (CHR$_6$)$_w$C$_5$-C$_6$ cycloalkenyl, CH$_2$(CHR$_6$)$_w$C$_5$-C$_6$ cycloalkenyl, C$_2$-C$_6$ alkenyl, or C$_2$-C$_6$ alkynyl.

In another embodiment, this invention provides a compound of formula IA-2 wherein R$_5$ is C$_1$-C$_6$ alkyl or (CHR$_6$)$_w$C$_3$-C$_6$ cycloalkyl.

In another embodiment, this invention provides a compound of formula IA-3, wherein R$_5$ is C$_1$-C$_6$ alkyl or (CHR$_6$)$_w$C$_3$-C$_6$ cycloalkyl.

In another embodiment, this invention provides a compound of formula IA-2, wherein R$_1$ is halogen or trifluoromethyl and R$_2$ is H or R$_1$ and R$_2$, on adjacent carbon atoms, are, independently, halogen or trifluoromethyl; and R$_5$ is C$_1$-C$_6$ alkyl or (CHR$_6$)$_w$C$_3$-C$_6$ cycloalkyl.

In another embodiment, this invention provides a compound of formula IA-3, wherein R$_1$ is halogen or trifluoromethyl and R$_2$ is H or R$_1$ and R$_2$, on adjacent carbon atoms, are, independently, halogen or trifluoromethyl; and R$_5$ is C$_1$-C$_6$ alkyl or (CHR$_6$)$_w$C$_3$-C$_6$ cycloalkyl.

In another embodiment, this invention provides a compound of formula IA-2, wherein R$_1$ and R$_2$ are, independently, methyl, methoxy, trifluoromethyl, F, Cl, or H; and R$_5$ is C$_1$-C$_6$ alkyl or (CHR$_6$)$_w$C$_3$-C$_6$ cycloalkyl.

In another embodiment, this invention provides a compound of formula IA-3, wherein R$_1$ and R$_2$ are, independently, methyl, methoxy, trifluoromethyl, F, Cl, or H; R' is H; and R$_5$ is C$_1$-C$_6$ alkyl or (CHR$_6$)$_w$C$_3$-C$_6$ cycloalkyl.

In another embodiment, this invention provides a compound of formula IA-1 or IA-2 or IA-3, wherein R$_1$ is halogen, C$_1$-C$_6$ alkyl, mono-halo C$_1$-C$_6$ alkyl, CN, di-halo C$_1$-C$_6$ alkyl, CF$_3$, CN, or O—C$_1$-C$_6$ alkyl; R' is methyl or ethyl; and R$_5$ is C$_5$-C$_6$ alkyl or CH$_2$—C$_3$-C$_6$ cycloalkyl.

In another embodiment, this invention provides a compound of formula IA-1 or IA-2 or IA-3, wherein R$_1$ is H, halogen, cyano, CF$_3$, or methoxy, R$_2$ is H, F, or methyl, R' is H, halogen, methyl, ethyl, or methoxy, and R$_5$ is C$_5$-C$_6$ alkyl or CH$_2$—C$_3$-C$_6$ cycloalkyl.

In another embodiment, this invention provides a compound of formula I, wherein R$_1$ is F, Cl, or CF$_3$; R$_2$ is H; and R' is halogen, methyl, ethyl, or methoxy; R$_3$ and R$_4$ are H, methyl, or Cl; and R$_5$ is C$_5$-C$_6$ alkyl or CH$_2$—C$_3$-C$_6$ cycloalkyl.

In another embodiment, this invention provides a compound of formula I, wherein R$_1$ is halogen or CF$_3$; R$_2$ is H, F, or methyl, R' is phenyl; R$_3$ and R$_4$ are H, methyl, or Cl; and R$_5$ is C$_5$-C$_6$ alkyl or CH$_2$—C$_5$-C$_6$ cycloalkyl.

In another embodiment, this invention provides a compound of formula I, wherein R$_1$ is halogen or CF$_3$; R$_2$ is H, F, or methyl, R' is halophenyl; R$_3$ and R$_4$ are H, methyl, or Cl; and R$_5$ is C$_5$-C$_6$ alkyl or CH$_2$—C$_5$-C$_6$ cycloalkyl.

In another embodiment, this invention provides a compound of formula I, wherein R$_1$ is NH$_2$, NH—C$_1$-C$_6$ alkyl; N(C$_1$-C$_6$ alkyl)-C$_1$-C$_6$ alkyl, NHC(=O)C$_1$-C$_6$ alkyl, C(=O)N(CH$_3$)$_2$, C(=O)N(Et)$_2$, C(=O)NH$_2$, C(=O)NH—C$_1$-C$_6$ alkyl, SO$_2$NH$_2$, NHSO$_2$—C$_1$-C$_6$ alkyl.

In another embodiment, this invention provides a compound of formula I wherein R$_1$ is NH$_2$, NH—C$_1$-C$_6$ alkyl; or N(C$_1$-C$_6$ alkyl)-C$_1$-C$_6$ alkyl; and R$_2$ is H or halogen.

In another embodiment, this invention provides a compound of formula I wherein R$_1$ is NHC(=O)C$_1$-C$_6$ alkyl, C(=O)N(CH$_3$)$_2$, C(=O)N(Et)$_2$, C(=O)NH$_2$, or C(=O)NH—C$_1$-C$_6$ alkyl.

In another embodiment, this invention provides a compound of formula 1 wherein R$_1$ is NHC(=O)C$_1$-C$_6$ alkyl, C(=O)N(CH$_3$)$_2$, C(=O)N(Et)$_2$, C(=O)NH$_2$, or C(=O)NH—C$_1$-C$_6$ alkyl.

In another embodiment, this invention provides a compound of formula 1 wherein R$_1$ is SO$_2$NH$_2$ or NHSO$_2$—C$_1$-C$_6$ alkyl.

In another embodiment, this invention provides a compound of formula IA-2 wherein R$_1$ is SO$_2$NH$_2$ or NHSO$_2$—C$_1$-C$_6$ alkyl.

In another embodiment, this invention provides a compound of formula I, wherein R$_1$ is C(=O)OC$_1$—C$_6$ alkyl, OC(=O)C$_1$-C$_6$ alkyl, OC$_1$-C$_6$ alkyl, or SC$_1$-C$_6$ alkyl.

In another embodiment, this invention provides a compound of formula I, wherein R$_1$ is (CH$_2$)$_m$C$_3$-C$_6$ cycloalkenyl, C$_2$-C$_6$ alkenyl, or C$_2$-C$_6$ alkynyl.

In another embodiment, this invention provides a compound of formula I, wherein R$_1$ is CH$_2$OCH$_3$, CH$_2$OCH$_2$CH$_3$, OC$_1$-C$_6$ alkyl, or SC$_1$-C$_6$ alkyl.

In another embodiment, this invention provides a compound of formula IA-1, wherein R$_1$ is C(=O)OC$_1$-C$_6$ alkyl, OC(=O)C$_1$-C$_6$ alkyl, OC$_1$-C$_6$ alkyl, or SC$_1$-C$_6$ alkyl.

In another embodiment, this invention provides a compound of formula IA-1, wherein R$_1$ is CH$_2$OCH$_3$, CH$_2$OCH$_2$CH$_3$, OC$_1$-C$_6$ alkyl, or SC$_1$-C$_6$ alkyl.

In another embodiment, this invention provides a compound of formula IA-1, wherein R$_1$ is C(=O)OC$_1$-C$_6$ alkyl, OC(=O)C$_1$-C$_6$ alkyl, OC$_1$-C$_6$ alkyl, or SC$_1$-C$_6$ alkyl; R$_2$ is H, F, or methyl, R' is halogen or methyl; and R$_5$ is C$_5$-C$_6$ alkyl or CH$_2$—C$_5$-C$_6$ cycloalkyl.

In another embodiment, this invention provides a compound of formula IA-1, wherein R$_1$ is NH$_2$, NH—C$_1$-C$_6$ alkyl; or $N(C_1\text{-}C_6\text{ alkyl})\text{-}C_1\text{-}C_6$ alkyl; $R_2$ is H, F, or methyl, $R_1$ is halogen or methyl; and $R_5$ is $C_5\text{-}C_6$ alkyl or $CH_2\text{---}C_5\text{-}C_6$ cycloalkyl.

In another embodiment, this invention provides a compound of formula IA-1, wherein $R_1$ is $NHC(\!\!=\!\!O)C_1\text{-}C_6$ alkyl, $C(\!\!=\!\!O)N(CH_3)_2$, $C(\!\!=\!\!O)N(Et)_2$, $C(\!\!=\!\!O)NH_2$, $C(\!\!=\!\!O)NH\text{---}C_1\text{-}C_6$ alkyl, $SO_2NH_2$, or $NHSO_2\text{---}C_1\text{-}C_6$ alkyl; $R_2$ is H, F, or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula I, wherein $R_1$ is $C_2\text{-}C_6$ alkynyl, optionally substituted.

In another embodiment, this invention provides a compound of formula I, wherein $R_1$ and $R_2$ form a fused, nitrogen-containing ring.

In another embodiment, this invention provides a compound of formula I, wherein $R_1$ and $R_2$ form a fused, oxygen-containing ring.

In another embodiment, this invention provides a compound of formula I, wherein $R_1$ and $R_2$ form a fused thiazolo or isothiazolo group.

In another embodiment, this invention provides a compound of formula I, wherein $R_1$ and $R_2$ form a fused cyclopentane, optionally substituted.

In another embodiment, this invention provides a compound of formula I, wherein $R_1$ and $R_2$ form a fused cyclohexane, optionally substituted.

In another embodiment, this invention provides a compound of formula IA-1 or IA-2, wherein $R_1$ and $R_2$ form a fused, nitrogen-containing ring.

In another embodiment, this invention provides a compound of formula IA-1 or IA-2, wherein $R_1$ and $R_2$ form a fused, oxygen-containing ring.

In another embodiment, this invention provides a compound of formula IA-1 or IA-2, wherein $R_1$ and $R_2$ form a fused thiazolo or isothiazolo group.

In another embodiment, this invention provides a compound of formula IA-1 or IA-2, wherein $R_1$ and $R_2$ form a fused cyclopentane, optionally substituted.

In another embodiment, this invention provides a compound of formula IA-1 or IA-2, wherein $R_1$ and $R_2$ form a fused cyclohexane, optionally substituted.

In another embodiment, this invention provides a compound of formula IA-1 or IA-2, wherein $R_1$ and $R_2$ form a fused, nitrogen-containing ring; and $R_5$ is $C_5\text{-}C_6$ alkyl or $CH_2\text{---}C_5\text{-}C_6$ cycloalkyl.

In another embodiment, this invention provides a compound of formula IA-1 or IA-2, wherein $R_1$ and $R_2$ form a fused, oxygen-containing ring; and $R_5$ is $C_5\text{-}C_6$ alkyl or $CH_2\text{---}C_5\text{-}C_6$ cycloalkyl.

In another embodiment, this invention provides a compound of formula IA-1 or IA-2, wherein $R_1$ and $R_2$ form a fused thiazolo or isothiazolo group; and $R_5$ is $C_5\text{-}C_6$ alkyl or $CH_2\text{---}C_5\text{-}C_6$ cycloalkyl.

In another embodiment, this invention provides a compound of formula IA-1 or IA-2, wherein $R_1$ and $R_2$ form a fused cyclopentane, optionally substituted; and $R_5$ is $C_5\text{-}C_6$ alkyl or $CH_2\text{---}C_5\text{-}C_6$ cycloalkyl.

In another embodiment, this invention provides a compound of formula IA-1 or IA-2, wherein $R_1$ and $R_2$ form a fused cyclohexane, optionally substituted; and $R_5$ is $C_5\text{-}C_6$ alkyl or $CH_2\text{---}C_5\text{-}C_6$ cycloalkyl.

In another embodiment, this invention provides a compound of formula IA-1, wherein $R_1$ is halogen; $R_2$ is H, F, or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-1, wherein $R_1$ is halogen; $R_2$ is H, F, or methyl, R' is 2-(dimethylamino) ethyl; and $R_5$ is $C_5\text{-}C_6$ alkyl or $CH_2\text{-}C_5\text{-}C_6$ cycloalkyl.

In another embodiment, this invention provides a compound of formula IA-1, wherein $R_1$ is halogen; $R_2$ is H, halogen, or methyl, R' is H; and $R_5$ is $C_5\text{-}C_6$ alkyl or $CH_2\text{---}C_5\text{-}C_6$ cycloalkyl.

In another embodiment, this invention provides a compound of formula IA-2, wherein $R_1$ is halogen; $R_2$ is H or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-1, wherein $R_1$ is Br, Cl, F or methyl; $R_2$ is H or F and $R_5$ is t-butyl or cyclopentylmethyl.

In another embodiment, this invention provides a compound of formula IA-1, wherein $R_1$ is trifluoromethyl; $R_2$ is H or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-2, wherein $R_1$ wherein $R_1$ is trifluoromethyl; $R_2$ is H or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-3, wherein $R_1$ wherein $R_1$ is trifluoromethyl; $R_2$ is H or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-1 or IA-2, wherein $R_1$ wherein $R_1$ is trifluoromethyl; $R_2$ is H or methyl, R' is halogen or methyl; and $R_5$ is $C_5\text{-}C_6$ alkyl or $CH_2\text{---}C_5\text{-}C_6$ cycloalkyl.

In another embodiment, this invention provides a compound of formula IA-2, wherein $R_1$ is trifluoromethyl; $R_2$ is F; R' is halogen or methyl; and $R_5$ is $C_5\text{-}C_6$ alkyl or $CH_2\text{---}C_5\text{-}C_6$ cycloalkyl.

In another embodiment, this invention provides a compound of formula I, wherein $R_1$ or $R_5$ is $CH_2Ar$ or $CH_2CH_2\text{---}Ar$, wherein Ar is phenyl, pyridyl, pyrrolyl, imidazolyl, oxazolyl, or thiazolyl.

In another embodiment, this invention provides a compound of formula I, wherein $R_1$ is F.

In another embodiment, this invention provides a compound of formula I, wherein $R_1$ is Cl.

In another embodiment, this invention provides a compound of formula I, wherein $R_1$ is Br.

In another embodiment, this invention provides a compound of formula IA-1, wherein $R_1$ is F.

In another embodiment, this invention provides a compound of formula IA-1, wherein $R_1$ is Cl.

In another embodiment, this invention provides a compound of formula IA-1, wherein $R_1$ is Br.

In another embodiment, this invention provides a compound of formula IA-1, wherein $R_1$ is F and $R_2$ is H, $OCH_3$, or F.

In another embodiment, this invention provides a compound of formula IA-1, wherein $R_1$ is F; $R_3$ and $R_4$ are both methyl; and R' is H.

In another embodiment, this invention provides a compound of formula IA-1, wherein $R_1$ is $CF_3$; $R_3$ and $R_4$ are both methyl; and R' is H.

In another embodiment, this invention provides a compound of formula I, wherein $R_1$ and $R_2$ are both F.

In another embodiment, this invention provides a compound of formula I, wherein $R_1$ is mono-, di-, or tri-halomethyl.

In another embodiment, this invention provides a compound of formula I, wherein $R_1$ is $CH_2F$, $CHF_2$, or $CF_3$.

In another embodiment, this invention provides a compound of formula I, wherein $R_1$ is $CH_2Cl$.

In another embodiment, this invention provides a compound of formula I, wherein $R_1$ is $CH_2Br$.

In another embodiment, this invention provides a compound of formula IA-1, wherein $R_1$ and $R_2$ are both F; $R_3$ and $R_4$ are both methyl; and R' is H.

In another embodiment, this invention provides a compound of formula IA-2, wherein $R_1$ is F.

In another embodiment, this invention provides a compound of formula IA-2, wherein $R_1$ and $R_2$ are both F.

In another embodiment, this invention provides a compound of formula IA-3, wherein $R_1$ is F.

In another embodiment, this invention provides a compound of formula IA-3, wherein $R_1$ and $R_2$ are both F.

In another embodiment, this invention provides a compound of formula I, wherein $R_1$ or $R_5$ is $CH_2Ar$ or $CH_2CH_2$—Ar, wherein Ar is isoxazolyl or isothiazolyl.

In another embodiment, this invention provides a compound of formula I, wherein $R_1$ or $R_5$ is $CH_2Ar$ or $CH_2CH_2$—Ar, wherein Ar is quinolyl or isoquinolyl.

In another embodiment, this invention provides a compound of formula I, wherein $R_1$ or $R_5$ is $CH_2Ar$ or $CH_2CH_2$—Ar, wherein Ar is pyrimidyl or purinyl.

In another embodiment, this invention provides a compound of formula I, wherein $R_1$ or $R_5$ is $CH_2Ar$ or $CH_2CH_2$—Ar, wherein Ar is indolyl, isoindolyl, or benzimidazolyl.

In an embodiment, this invention provides a compound of formula I, wherein $R_1$ or $R_5$ is $CH_2Ar$ or $CH_2CH_2$—Ar, wherein Ar is halo phenyl.

In another embodiment, this invention provides a compound of formula I, wherein $R_1$ or $R_5$ is $CH_2Ar$ or $CH_2CH_2$—Ar, wherein Ar is dihalophenyl or dihalopyridyl.

In another embodiment, invention provides a compound of formula I, wherein $R_1$ or $R_5$ is $CH_2Ar$ or $CH_2CH_2$—Ar, wherein Ar is mono- or di-halothienyl, mono- or di-halofuryl, mono- or di-halobenzothienyl, or mono- or di-halobenzofuryl.

In another embodiment, this invention provides a compound of formula I, wherein $R_1$ or $R_5$ is $CH_2Ar$ or $CH_2CH_2$—Ar, wherein Ar is o-, m-, or p-xylyl or o-, m-, or p-anisyl.

In another embodiment, this invention provides a compound of formula I, wherein $R_1$ or $R_5$ is $CH_2Ar$ or $CH_2CH_2$—Ar, wherein Ar is m- or p-cyanophenyl or m- or p-cyanomethyl phenyl.

In another embodiment, this invention provides a compound of formula I, in which $R_3$ and R4 are halogen, $CF_3$, or $C_1$-$C_3$ alkyl and $R_5$ is $C_1$-$C_6$ alkyl, wherein the alkyl group is substituted with one or two groups selected, independently, from OH, OMe, OEt, F, $CF_3$, Cl, or CN.

In another embodiment, this invention provides a compound of formula I, in which $R_3$ and $R_4$ are halogen, $CF_3$, $OCF_3$, $C_1$-$C_3$ alkyl, or $OC_1$-$C_3$ alkyl, and $R_5$ is $(CH_2)_w C_3$-$C_6$ cycloalkyl, wherein w is 1 or 2, wherein the cycloalkyl group is substituted with Me, OH, OMe, OEt, F, $CF_3$, Cl, or CN.

In an embodiment, this invention provides a compound of formula IA-1, in which $R_3$ and $R_4$ are halogen, $CF_3$, or $C_1$-$C_3$ alkyl, and $R_5$ is $(CH_2)_w$—$C_5$-$C_6$ cycloalkyl, optionally substituted, or $(CH_2)_w$—$C_5$-$C_6$ heterocycloalkyl, optionally substituted.

In another embodiment, this invention provides a compound of formula IA-1, wherein $R_1$ is $CH_2$phenyl or $CH_2CH_2$-phenyl.

In another embodiment, this invention provides a compound of formula IA-1, wherein $R_1$ is Ar, $CH_2Ar$ or $CH_2CH_2$—Ar, wherein Ar is 3,5-dichlorophenyl or 3,5-difluorophenyl.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl; $R_3$ and $R_4$ are H or $C_1$-$C_6$ alkyl, unsubstituted or substituted with one or two groups selected from OH, OMe; and $R_6$ is CN, $CH_2CN$, or halogen.

In another embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl; and $R_1$ is F, $CH_2F$, $CHF_2$, $CF_3$, or $CF_2CF_3$.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $OC_1$-$C_6$ alkyl or $C(=O)C_1$-$C_6$ alkyl.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $C(=O)OC_1$-$C_6$ alkyl or $OC(=O)C_1$-$C_6$ alkyl.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl, $R_1$ is $C_2$-$C_6$ alkenyl or $C_2$-$C_6$ alkynyl, q is 1, and X and Y are both O.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, Ar is phenyl or pyridyl, and $R_1$ is $SC_1$-$C_6$ alkyl.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl, $R_3$ and $R_4$ are H, Cl, methoxy, or $C_1$-$C_3$ alkyl, and $R_1$ is $C_1$-$C_6$ alkyl.

In an embodiment, this invention provides a compound of formula IA-2, wherein $R_5$ is Ar, $(CHR_6)_w Ar$, $CH_2(CHR_6)_w Ar$, or $(CHR_6)_w CH_2 Ar$, wherein Ar is phenyl or pyridyl; $R_3$ and $R_4$ are H, Cl, methoxy, or $C_1$-$C_2$ alkyl, unsubstituted or substituted with one or two groups selected from OH, OMe; and $R_1$ is CN, $CH_2CN$, or halogen.

In another embodiment, this invention provides a compound of formula IA-2, wherein $R_5$ is Ar, $(CHR_6)_w Ar$, $CH_2(CHR_6)_w Ar$, or $(CHR_6)_w CH_2 Ar$, wherein Ar is phenyl or pyridyl; and $R_1$ is F, $CH_2F$, $CHF_2$, $CF_3$, or $CF_2CF_3$.

In an embodiment, this invention provides a compound of formula IA-1, wherein $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $OC_1$-$C_6$ alkyl or $C(=O)C_1$-$C_6$ alkyl.

In an embodiment, this invention provides a compound of formula IA-2, wherein $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $OC_1$-$C_6$ alkyl or $C(=O)C_1$-$C_6$ alkyl.

In an embodiment, this invention provides a compound of formula IA-3, wherein $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $OC_1$-$C_6$ alkyl or $C(=O)C_1$-$C_6$ alkyl.

In an embodiment, this invention provides a compound of formula IA-3, wherein R' is phenyl or methoxy, $R_2$ is H, and $R_5$ is Ar, $(CHR_6)_w Ar$, $CH_2(CHR_6)_w Ar$, or $(CHR_6)_w CH_2 Ar$, wherein Ar is phenyl or pyridyl, and $R_1$ is $C(=O)OC_1$-$C_6$ alkyl or $OC(=O)C_1$-$C_6$ alkyl.

In an embodiment, this invention provides a compound of formula IA-2, wherein $R_5$ is Ar, $(CHR_6)_w Ar$, $CH_2(CHR_6)_w Ar$, or $(CHR_6)_w CH_2 Ar$, Ar is phenyl or pyridyl, and $R_1$ is $SC_1$-$C_6$ alkyl.

In an embodiment, this invention provides a compound of formula IA-2, wherein $R_5$ is Ar, $(CHR_6)_w Ar$, $CH_2(CHR_6)_w Ar$, or $(CHR_6)_w CH_2 Ar$, wherein Ar is phenyl or pyridyl, $R_3$ and $R_4$ are H or $C_1$-$C_3$ alkyl, and $R_1$ is $C_1$-$C_6$ alkyl.

In another embodiment, this invention provides a method of treating or preventing a disease, disorder, or condition that is affected by modulation of potassium ion channels in a patient comprising administration of a compound of formula I in an amount of up to about 2000 mg per day.

In another embodiment, this invention provides a method of treating or preventing a disease, disorder, or condition that is affected by modulation of potassium ion channels in a patient comprising administration of a compound of formula I in an amount of from about 10 mg to about 2000 mg per day.

In another embodiment, this invention provides a method of treating or preventing a disease, disorder, or condition that is affected by modulation of potassium ion channels in a patient comprising administration of a compound of formula IA-1 in an amount of up to about 2000 mg per day.

In another embodiment, this invention provides a method of treating or preventing a seizure disorder in a patient comprising administration of a compound of formula I in an amount of up to about 2000 mg per day.

In another embodiment, this invention provides a method of treating or preventing a seizure disorder in a patient comprising administration of a compound of formula I in an amount of from about 10 mg per day to about 2000 mg per day.

In another embodiment, this invention provides a method of treating or preventing a seizure disorder in a patient comprising administration of a compound of formula I in an amount of from about 300 mg per day to about 2000 mg per day.

In another embodiment, this invention provides a method of treating or preventing a seizure disorder in a patient comprising administration of a compound of formula I in an amount of from about 300 mg per day to about 1200 mg per day.

In another embodiment, this invention provides a method of treating or preventing a seizure disorder in a patient comprising administration of a compound of formula IA-1 in an amount of up to 2000 mg per day.

In another embodiment, this invention provides a method of treating or preventing a seizure disorder in a patient comprising administration of a compound of formula IA-1 in an amount of from about 10 mg per day to about 2000 mg per day.

In another embodiment, this invention provides a method of treating or preventing a seizure disorder in a patient comprising administration of a compound of formula IA-1 in an amount of from about 300 mg per day to about 2000 mg per day.

In another embodiment, this invention provides a method of treating or preventing a seizure disorder in a patient comprising administration of a compound of formula IA-1 in an amount of from about 300 mg per day to about 1200 mg per day.

DETAILED DESCRIPTION OF INVENTION

As provided by this invention, compounds of formula IA are designed for oral or intravenous dosing of up to 2000 mg per day. Yet the high activities of many of these compounds indicate that dosing of less than 1200 mg per day—the current anticipated dosing level of retigabine in adults—is possible. Thus, this invention comprises tablets, capsules, solutions, and suspensions of compounds of formula IA which are formulated for oral administration. Similarly, solutions and suspensions suitable for oral pediatric administration, comprising, in addition to compounds of formula IA, a syrup such as sorbitol or propylene glycol, among many other examples, are also contemplated. ally, solutions and suspensions comprising, in addition to compounds of formula IA, a syrup such as sorbitol or propylene glycol, along with colorants and flavorings suitable for oral pediatric administration, are also contemplated. Additionally, both chewable and non-chewable tablets comprising compounds of formula IA, along with pharmaceutically acceptable tabletting agents and other pharmaceutically acceptable carriers and excipients, are also contemplated. As used herein, the term pharmaceutically acceptable carrier comprises such excipients, binders, lubricants, tabletting agents, disintegrants, preservatives, anti-oxidants, flavours and colourants as are typically used in the art of formulation of pharmaceuticals. Examples of such agents include—but are not limited to—starch, calcium carbonate, dibasic calcium phosphate, dicalcium phosphate, microcrystalline cellulose, hydroxypropylcellulose, hydroxypropylmethylcellulose lactose, polyethylene glycols, polysorbates, glycols, safflower oil, sesame oil, soybean oil, and Povidone. Additionally, disintegrants such as sodium starch glycolate; lubricants such as magnesium stearate, stearic acid, and $SiO_2$; and solubility enhancers such as cyclodextrins, among a great many other examples for each group, are contemplated. Such materials and the methods of using them are well known in the pharmaceutical art. Additional examples are provided in Kibbe, *Handbook of Pharmaceutical Excipients*, London, Pharmaceutical Press, 2000.

As used herein, the term "pharmaceutically acceptable acid salts" refers to acid addition salts formed from acids which provide non-toxic anions. The pharmaceutically acceptable anions include, but are not limited to, acetate, aspartate, benzoate, bicarbonate, carbonate, bisulfate, sulfate, chloride, bromide, benzene sulfonate, methyl sulfonate, phosphate, acid phosphate, lactate, maleate, malate, malonate, fumarate, lactate, tartrate, borate, camsylate, citrate, edisylate, esylate, formate, fumarate, gluceptate, glucuronate, gluconate oxalate, palmitate, pamoate, saccharate, stearate, succinate, tartrate, tosylate and trifluoroacetate salts, among a great many other examples. Hemi-salts, including but not limited to hemi-sulfate salts, are likewise contemplated.

For a review on suitable salts, see "Handbook of Pharmaceutical Salts: Properties, Selection, and Use" by Stahl and Wermuth (Wiley-VCH, Weinheim, Germany, 2002).

As is well known, pharmaceutically acceptable salts of compounds of formula I may be prepared by reaction of a compound of formula I with the desired acid; by removal of a protecting group from a suitable precursor of the compound of formula I or by ring-opening a suitable cyclic precursor, for example, a lactone or lactam, using the desired acid or base; and by conversion of one salt of the compound of formula I to another by reaction with an appropriate acid or base or by passage through an appropriate ion-exchange column.

As used herein, the term "pharmaceutically acceptable solvate" refers to describe a molecular complex comprising the compound of the invention and a stoichiometric amount of one or more pharmaceutically acceptable solvent molecules, including but not limited to water and ethanol. Thus, the term solvate includes a hydrate as one example and an ethanolate as another example.

The compounds of the present invention may possess one or more asymmetric carbons. Accordingly, any optical isomers as separated and any mixtures including racemic mixtures are embraced by the scope of the present invention. Resolution of racemic mixtures can be accomplished by methods known to those skilled in the art.

The compounds of the present invention may also exist as geometric isomers and in different tautomeric forms. Those geometric isomers and tautomeric forms are included within the scope of the present invention.

As used herein, modulation of ion channels refers to activating the ion channels, to affecting the kinetics of opening and closing of the ion channels, or to causing any change in the channel open probability of the ion channels.

Preparation of Compounds

The Preparation of Compounds of Formula I is Outlined in Schemes I and II

Scheme I

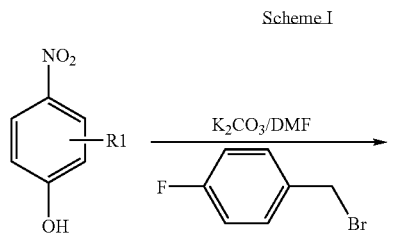

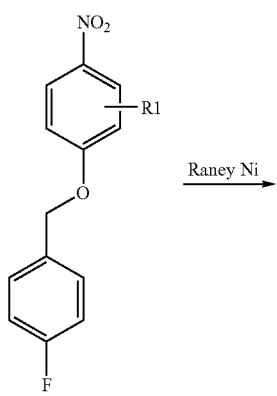

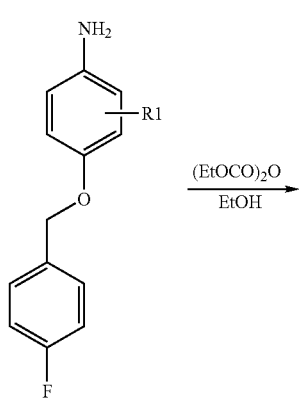

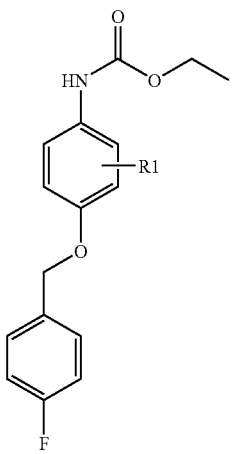

While in the above Scheme I nitrophenol is exemplified, a great many substituted nitrophenols are known and are therefore embraced by Scheme I. Thus, for example, compounds of Formula I wherein $R_3$ and $R_4$ are $CF_3$, $OCF_3$, $OC_1$-$C_3$ alkyl or $C_1$-$C_3$ alkyl or $C_1$-$C_3$ alkyl can be prepared from the appropriate substituted nitrophenol starting material. Likewise the exemplified flurobenzylchloride of Scheme I can be replaced by a number of other substituted benzyl chloride. For example, if the compounds of Formula I wherein $R_1$ and $R_2$ are independently selected from $C_1$-$C_6$ alkyl, $C_3$-$C_6$ cycloalkyl or $OC_1$-$C_6$ alkyl can be prepared from the appropriate substituted benzyl chloride starting material. It is to be understood that while the benzyl chloride of Scheme I is substituted by a single R group, a second R group which would correspond to the $R_1$ and $R_2$ groups of Formula I is included.

While Scheme I exemplifies the preparation of a substituted carbamic acid ethyl ester wherein the ethyl group would correspond to the $R_5$ position of Formula I, it is to be understood that substitution of the appropriate reagent for the diethyl pyrocarbonate of Scheme I would yield the corresponding moiety which is defined by $R_5$.

1-nitro-4-(4-fluorobenzyloxy)-benzene

A mixture of 4-nitrophenol (1.39 g, 10 mmol), potassium carbonate (1.38 g, 10 mmol) and 4-fluorobenzyl bromide (1.89 g, 10 mmol) in 20 ml of anhydrous DMF was stirred at 100° C. for 2 days. After cooling to room temperature, the reaction mixture was poured into 200 ml of ice-water with stirring. The solid was filtered and washed with water and dried to give 2.37 g (96%) of 1-nitro-4-(4-fluorobenzyloxy)-benzene as yellow solids.

The following compounds were synthesized by the same procedure:

1-Nitro-2-fluoro-4-(4-fluorobenzyloxy)-benzene, yellow solids, 96%

1-Nitro-2-methyl-4-(4-fluorobenzyloxy)-benzene, yellow solids, 97%

1-Nitro-2-trifluoromethyl-4-(4-fluorobenzyloxy)-benzene, yellow solids, 95%

1-Nitro-3-fluoro-4-(4-fluorobenzyloxy)-benzene, yellow solids, 91%

1-Nitro-3-chloro-4-(4-fluorobenzyloxy)-benzene, yellow solids, 85%

1-Nitro-3-methoxy-4-(4-fluorobenzyloxy)-benzene, yellow solids, 97%

4-(4-Fluoro-benzyloxy)-aniline

1-Nitro-4-(4-fluorobenzyloxy)-benzene (2.37 g) was dissolved in 200 ml of methanol and catalytic amount of Raney Ni was added. The mixture was stirred at room temperature under atmospheric pressure in a hydrogen atmosphere for 3 hours. After filtering off Raney Ni over Celite and washing with methanol, the obtained filtrate was concentrated under reduced pressure to give a solid product 4-(4-fluoro-benzyloxy)-aniline, which is pure enough for next step.

The following compounds were synthesized by the same procedure:
2-Fluoro-4-(4-Fluoro-benzyloxy)-aniline
2-Trifluoromethyl-4-(4-Fluoro-benzyloxy)-aniline
2-Methyl-4-(4-Fluoro-benzyloxy)-aniline
3-Fluoro-4-(4-Fluoro-benzyloxy)-aniline
3-Chloro-4-(4-Fluoro-benzyloxy)-aniline
3-Methoxy-4-(4-Fluoro-benzyloxy)-aniline.

[4-(4-Fluoro-benzyloxy)-phenyl]carbamic acid ethyl ester

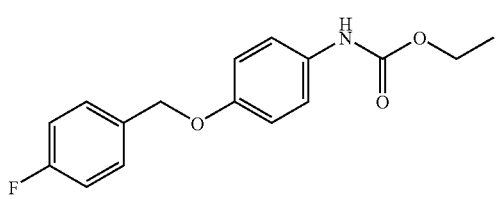

4-(4-Fluoro-benzyloxy)-aniline (0.22 g, 1 mmol) was dissolved in 8 ml of anhydrous ethanol and diethyl pyrocarbonate (0.20 g, 1.2 mmol) was added dropwise at room temperature. The resulting mixture was stirred at room temperature for 4 hours, then stored at −20° C. overnight. The crystals was filtered and washed with cold ethanol to give pure product as crystal solids (88 mg, 30%). The filtrate was concentrated to dryness under reduced pressure and the residue was purified by silica gel column to give another batch of pure products. $^1$H NMR (DMSO-$d_6$, 300 MHz): δ9.38 (brs, 1H, exchangeable with $D_2O$, NH), 7.46 (dd, J=5.7 and 8.1 Hz, 2H), 7.32 (d, J=8.7 Hz, 2H), 7.18 (t, J=8.7 Hz, 2H), 6.90 (d, J=8.7 Hz, 2H), 5.00 (s, 2H), 4.07 (q, J=7.2 Hz, 2H), 1.20 (t, J=7.2 Hz, 3H). MS: 288 (M−1).

The following compounds were synthesized by the same procedure:

[2-Methyl-4-(4-fluoro-benzyloxy)-phenyl]-carbamic acid ethyl ester

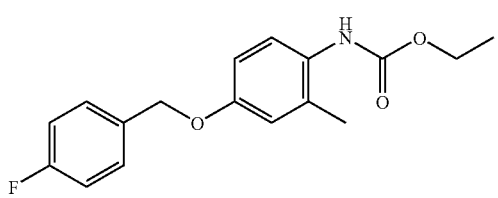

$^1$H NMR (DMSO-$d_6$, 300 MHz): δ 8.62 (brs, 1H, exchangeable with $D_2O$, NH), 7.46 (dd, J=5.7 and 8.1 Hz, 2H), 7.19 (t, J=8.7 Hz, 2H), 7.12 (d, J=8.7 Hz, 1H), 6.83 (d, J=2.7 Hz, 1H), 6.76 (dd, J=2.7 and 8.7 Hz, 1H), 5.02 (s, 2H), 4.04 (q, J=7.2 Hz, 2H), 2.12 (s, 3H), 1.19 (t, J=7.2 Hz, 3H). MS: 302 (M−1).

[2-Fluoro-4-(4-fluoro-benzyloxy)-phenyl]-carbamic acid ethyl ester

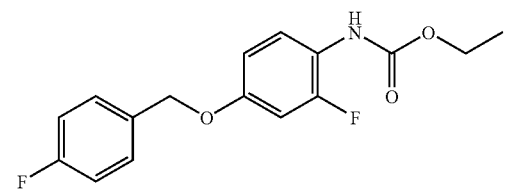

$^1$H NMR (DMSO-$d_6$, 300 MHz): δ 8.97 (brs, 1H, exchangeable with $D_2O$, NH), 7.47 (dd, J=5.7 and 8.1 Hz, 2H), 7.37 (t, J=8.7 Hz, 1H), 7.20 (t, J=8.7 Hz, 2H), 6.93 (dd, J=2.7 and 12.3 Hz, 1H), 6.78 (dd, J=2.7 and 8.7 Hz, 1H), 5.05 (s, 2H), 4.05 (q, J=7.2 Hz, 2H), 1.19 (t, J=7.2 Hz, 3H). MS: 307 (M−1).

[2-Trifluoromethyl-4-(4-fluoro-benzyloxy)-phenyl] carbamic acid ethyl ester

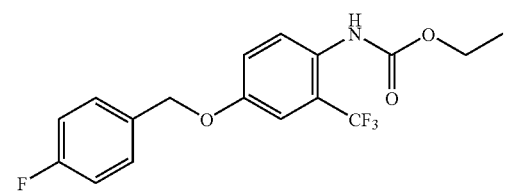

$^1$H NMR (DMSO-$d_6$, 300 MHz): δ 8.83 (brs, 1H, exchangeable with $D_2O$, NH), 7.50 (dd, J=5.7 and 8.1 Hz, 2H), 7.33 (d, J=8.7 Hz, 1H), 7.21 (t, J=8.7 Hz, 2H), 7.26 (dd, J=2.7 and 8.7 Hz, 1H), 7.24 (d, J=2.7 Hz, 1H), 5.15 (s, 2H), 4.03 (q, J=7.2 Hz, 2H), 1.16 (t, J=7.2 Hz, 3H). MS: 356 (M−1).

[3-Fluoro-4-(4-fluoro-benzyloxy)-phenyl]-carbamic acid ethyl ester

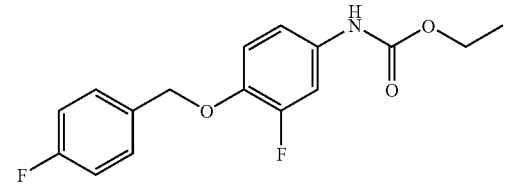

$^1$H NMR (DMSO-$d_6$, 300 MHz): δ 9.61 (brs, 1H, exchangeable with $D_2O$, NH), 7.46 (dd, J=5.7 and 8.1 Hz, 2H), 7.36 (dd, J=1.8 and 13.8 Hz, 1H), 7.20 (t, J=8.7 Hz, 2H), 7.16 (d, J=9.0 Hz, 1H), 7.09 (dd, J=1.8 and 9.0 Hz, 1H), 5.06 (s, 2H), 4.08 (q, J=7.2 Hz, 2H), 1.21 (t, J=7.2 Hz, 3H). MS: 306 (M−1).

[3-Chloro-4-(4-fluoro-benzyloxy)-phenyl]-carbamic acid ethyl ester

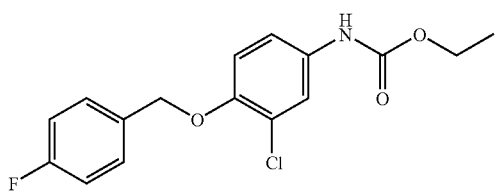

$^1$H NMR (DMSO-d$_6$, 300 MHz): δ 9.59 (brs, 1H, exchangeable with D$_2$O, NH), 7.55 (d, J=1.8 Hz, 1H), 7.48 (dd, J=5.7 and 8.7 Hz, 2H), 7.29 (dd, J=1.8 and 8.7 Hz, 1H), 7.21 (t, J=8.7 Hz, 2H), 7.15 (d, J=8.7 Hz, 1H), 5.10 (s, 2H), 4.08 (q, J=7.2 Hz, 2H), 1.21 (t, J=7.2 Hz, 3H). MS: 322 (M−1).

[3-Methoxy-4-(4-fluoro-benzyloxy)-phenyl]-carbamic acid ethyl ester

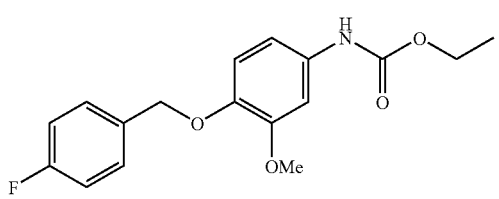

$^1$H NMR (DMSO-d$_6$, 300 MHz): δ 9.40 (brs, 1H, exchangeable with D$_2$O, NH), 7.45 (dd, J=5.7 and 8.4 Hz, 2H), 7.18 (t, J=8.7 Hz, 2H), 7.18 (m, 1H), 6.89 (m, 2H), 4.96 (s, 2H), 4.08 (q, J=7.2 Hz, 2H), 1.21 (t, J=7.2 Hz, 3H). MS: 318 (M−1).

Scheme II

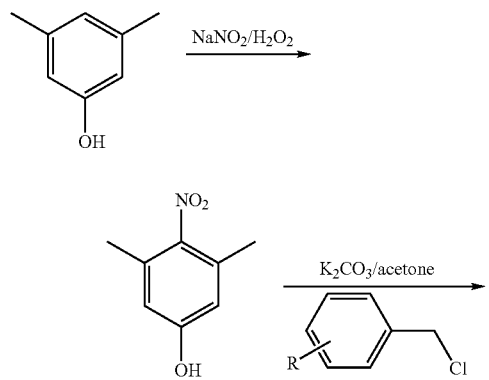

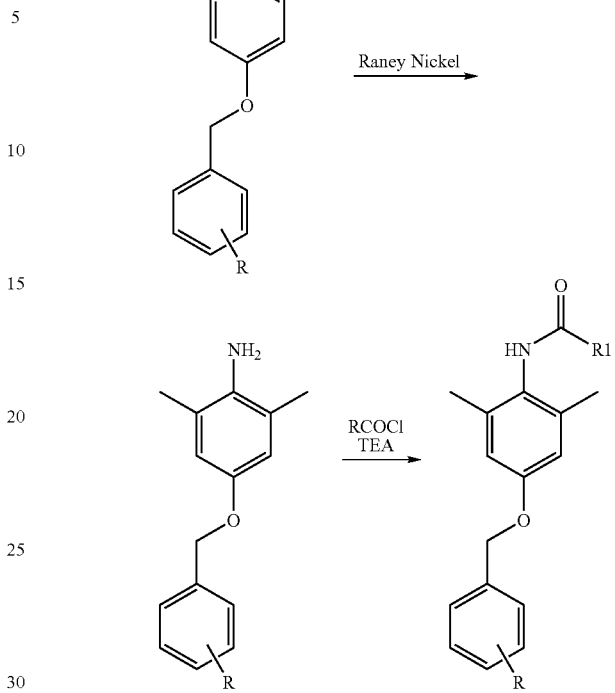

While in the above scheme II 3, 5-dimethylphenol is exemplified, a great many substituted phenols are known and are embraced by this scheme. Thus for example, compounds of formula I wherein R$_3$ and R$_4$ are CF$_3$, OCF$_3$ OC$_1$-C$_3$ alkyl or C$_1$-C$_3$ alkyl can be prepared from the appropriate substituted or disubstituted phenol starting material to arrive at the corresponding nitrophenol. Likewise the exemplified (fluoro)-benzyl chloride of the above scheme can be replaced by a number of other substituted benzyl chlorides. For example if compound of formula I wherein R$_1$ and R$_2$ are independently selected C$_1$-C$_3$ alkyl, C$_1$-C$_3$ cycloalkyl or OC$_1$-C$_6$ alkyl can be prepared from the appropriate substituted benzyl chloride starting material. It is to be understood that while the benzyl chloride of Scheme I is substituted by a single R group, a second R group which would correspond to the R$_1$ and R$_2$ groups of formula I is included.

In the above scheme II, R$_1$ of scheme II would correspond to R$_5$ of formula I and R would correspond to R$_1$ and R$_2$ of formula I.

3,5-Dimethyl-4-nitrophenol

[3,5-Dimethyl-4-nitrophenol was synthesized by the reference procedures (U.S. Pat. No. 4,564,640)] 750 ml of Concentrated hydrochloric acid was added to a solution of 3,5-dimethylphenol (80.6 g) in 750 ml of 95% ethanol. The mixture was cooled to 0° C. in an ice/methanol bath. While maintaining the temperature of the reaction mixture below 5° C., a solution of NaNO2 (69.0 g) in 150 ml of water was added dropwise to the reaction mixture. The mixture was stirred at 0° C. for more than an hour and then poured into 9 liters of water. The aqueous mixture was filtered to give a yellow solid which was recrystallized from hot methanol and filtered to give 71.45 g of 3,5-dimethyl-4-nitrosophenol as a yellow solid. Mp. 180-181° C.

A mixture of 3,5-dimethyl-4-nitrosophenol (70.63 g) from above and $(NH_4)_6Mo_7O_{24}\cdot 4H_2O)$ (2.83g) in 770 ml of glacial acetic acid was warmed to 100° C. 30% $H_2O_2$ (84 ml) was added to the mixture in 10 ml portions until an exothermic reaction was observed. The reaction mixture was then stirred and the remainder of the $H_2O_2$ solution added in small portions. The reaction mixture was heated and stirred until a clear dark red solution results. A yellow-orange solid precipitated from the solution after stirring for another 20-30 minutes. The reaction mixture was stirred overnight and filtered to give a small amount of a yellow solid and a clear dark red filtrate. The red filtrate was concentrated in vacuo and partitioned between water and ether. The aqueous layer was washed with ether and the combined ether extracts washed with 10% sodium carbonate until the aqueous layer becomes basic. The ether extract was dried over anhydrous sodium sulfate, filtered, concentrated and allowed to cool overnight. After cooling in an ice bath the mixture was filtered to give 49.5 g of 3,5-dimethyl-4-nitrophenol as a yellow-green solid. Mp. 106-108° C.

5-(4-Fluoro-benzyloxy)-2-nitro-meta-xylene

A mixture of 3,5-dimethyl-4-nitrophenol (0.97 g, 5.79 mmol), 4-fluorobenzyl chloride (1.26 g, 8.69 mmol) and anhydrous potassium carbonate (1.24 g, 9.0 mmol) in 50 ml of acetone was stirred under reflux for 22 hours. TLC showed this reaction is complete. The reaction mixture was cooled to room temperature and filtered and washed with acetone. The filtrate was evaporated to dryness to give the crude product, which was used for next step without further purification.

The following compounds were synthesized by the same procedure:

5-(4-Chloro-benzyloxy)-2-nitro-meta-xylene
5-(4-Bromo-benzyloxy)-2-nitro-meta-xylene
5-(4-Methyl-benzyloxy)-2-nitro-meta-xylene
5-(4-Trifluoromethyl-benzyloxy)-2-nitro-meta-xylene
5-(2-Trifluoromethyl-benzyloxy)-2-nitro-meta-xylene
5-(3-Trifluoromethyl-benzyloxy)-2-nitro-meta-xylene
5-(3-Chloro-benzyloxy)-2-nitro-meta-xylene
5-(3-Fluoro-benzyloxy)-2-nitro-meta-xylene
5-(2,4-Difluoro-benzyloxy)-2-nitro-meta-xylene
5-(3,4-Difluoro-benzyloxy)-2-nitro-meta-xylene 4-(4-Fluoro-benzyloxy)-2,6-dimethylaniline 1-Nitro-4-(4-fluorobenzyloxy)-benzene (0.5 g) was dissolved in 60 ml of methanol and catalytic amount of Raney Ni was added. The mixture was stirred at room temperature under atmospheric pressure in a hydrogen atmosphere for 3 hours. After filtering off Raney Ni over Celite and washing with methanol, the obtained filtrate was concentrated under reduced pressure to give a solid product 4-(4-fluoro-benzyloxy)-2,6-dimethylaniline, which is pure enough for next step.

The following compounds were synthesized by the same procedure:

4-(4-Chloro-benzyloxy)-2,6-dimethylaniline
4-(4-Bromo-benzyloxy)-2,6-dimethylaniline
4-(4-Methyl-benzyloxy)-2,6-dimethylaniline
4-(3,4-Difluoro-benzyloxy)-2,6-dimethylaniline
4-(2,4-Difluoro-benzyloxy)-2,6-dimethylaniline
4-(4-Trifluoromethyl-benzyloxy)-2,6-dimethylaniline
4-(3-Trifluoromethyl-benzyloxy)-2,6-dimethylaniline
4-(2-Trifluoromethyl-benzyloxy)-2,6-dimethylaniline
4-(3-Fluoro-benzyloxy)-2,6-dimethylaniline
4-(3-Chloro-benzyloxy)-2,6-dimethylaniline N-[4-(4-Fluoro-benzyloxy)-2,6-dimethyl-phenyl]-3,3-dimethyl-butyramide

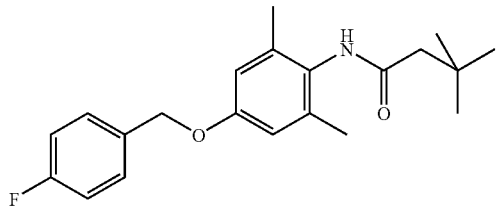

To a solution of 4-(4-fluoro-benzyloxy)-2,6-dimethylaniline(0.20 g, 0.82 mmol) from above and triethylamine (125 mg, 1.24 mmol) in anhydrous methylene chloride (20 ml) was added dropwise tert-butylacetyl chloride (135 mg, 1 mmol) at 0° C. The reaction mixture was stirred at room temperature for 18 hours. Water was added to the reaction mixture, and the mixture was washed with saturated brine and dried over sodium sulfate. The solvent was evaporated under reduced pressure. The residue was purified by silica gel column chromatography (ISCO, hexane/EtOAc, 0-40%, 40 min) and recrystallized from hexane/EtOAc (5:1) to give 230 mg (82%) of the white solids. $^1$H NMR (DMSO-$d_6$, 400 MHz): δ 8.92 (brs, 1H, exchangeable with $D_2O$, NH), 7.46 (dd, J=4.7 and 6.4 Hz, 2H), 7.19 (t, J=7.0 Hz, 2H), 6.70 (s, 2H), 5.02 (s, 2H), 2.16 (s, 2H), 2.08 (s, 6H), 1.03 (s, 9H). MS: 344 (M+1).

The following compounds were synthesized by the same procedure:

N-[4-(4-Chloro-benzyloxy)-2,6-dimethyl-phenyl]-3,3-dimethyl-butyramide

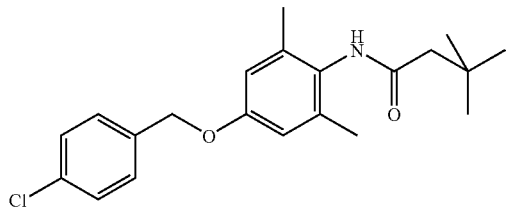

$^1$H NMR (DMSO-$d_6$, 400 MHz): δ 8.94 (brs, 1H, exchangeable with $D_2O$, NH), 7.46 (s, 4H), 6.72 (s, 2H), 5.07 (s, 2H), 2.18 (s, 2H), 2.10 (s, 6H), 1.05 (s, 9H). MS: 36 (M+1).

N-[4-(4-Bromo-benzyloxy)-2,6-dimethyl-phenyl]-3,3-dimethyl-butyramide

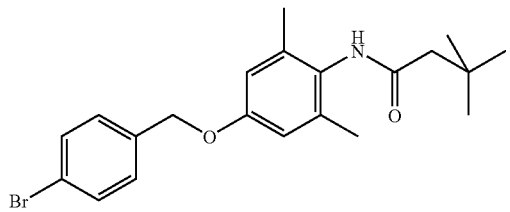

¹H NMR (DMSO-d₆, 400 MHz): δ 8.94 (brs, 1H, exchangeable with D₂O, NH), 7.59 (d, J=8.0 Hz, 2H), 7.39 (d, J=8.0 Hz, 2H), 6.71 (s, 2H), 5.05 (s, 2H), 2.18 (s, 2H), 2.10 (s, 6H), 1.05 (s, 9H). MS: 404 (M+1).

N-[4-(4-Methyl-benzyloxy)-2,6-dimethyl-phenyl]-3,3-dimethyl-butyramide

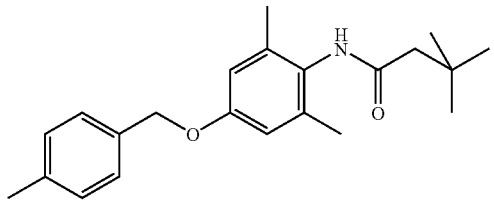

¹H NMR (DMSO-d₆, 400 MHz): δ 8.94 (brs, 1H, exchangeable with D₂O, NH), 7.30 (d, J=8.0 Hz, 2H), 7.20 (d, J=8.0 Hz, 2H), 6.70 (s, 2H), 5.01 (s, 2H), 2.31 (s, 3H), 2.18 (s, 2H), 2.09 (s, 6H), 1.05 (s, 9H). MS: 340 (M+1).

N-[4-(4-Trifluoromethyl-benzyloxy)-2,6-dimethyl-phenyl]-3,3-dimethyl-butyramide

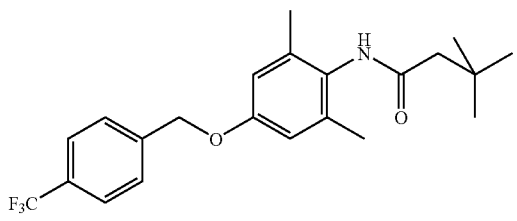

¹H NMR (DMSO-d₆, 400 MHz): δ 8.95 (brs, 1H, exchangeable with D₂O, NH), 7.76 (d, J=8.0 Hz, 2H), 7.66 (d, J=8.0 Hz, 2H), 6.74 (s, 2H), 5.19 (s, 2H), 2.18 (s, 2H), 2.10 (s, 6H), 1.05 (s, 9H). MS: 394 (M+1).

N-[4-(2-Trifluoromethyl-benzyloxy)-2,6-dimethyl-phenyl]-3,3-dimethyl-butyramide

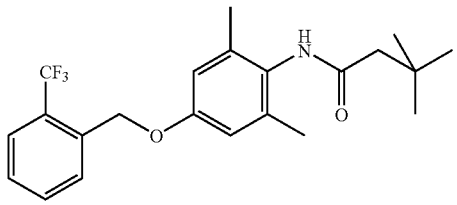

¹H NMR (DMSO-d₆, 400 MHz): δ 8.96 (brs, 1H, exchangeable with D₂O, NH), 7.80 (d, J=8.0 Hz, 1H), 7.74 (t, J=8.0 Hz, 1H), 7.71 (d, J=8.0 Hz, 1H), 7.59 (t, J=8.0 Hz, 1H), 6.72 (s, 2H), 5.19 (s, 2H), 2.19 (s, 2H), 2.11 (s, 6H), 1.05 (s, 9H). MS: 394 (M+1).

N-[4-(3-Trifluoromethyl-benzyloxy)-2,6-dimethyl-phenyl]-3,3-dimethyl-butyramide

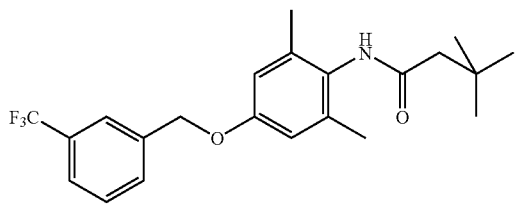

¹H NMR (DMSO-d₆, 400 MHz): δ 8.96 (brs, 1H, exchangeable with D₂O, NH), 7.80 (s, 1H), 7.75 (d, J=8.0 Hz, 1H), 7.70 (d, J=8.0 Hz, 1H), 7.64 (t, J=8.0 Hz, 1H), 6.75 (s, 2H), 5.18 (s, 2H), 2.19 (s, 2H), 2.11 (s, 6H), 1.05 (s, 9H). MS: 394 (M+1).

N[4-(3-Chloro-benzyloxy)-2,6-dimethyl-phenyl]-3,3-dimethyl-butyramide

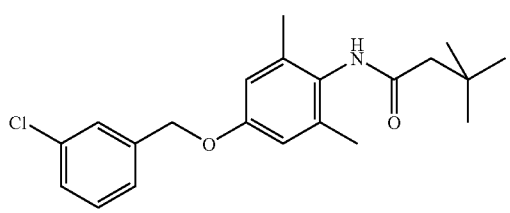

¹H NMR (DMSO-d₆, 400 MHz): δ 8.94 (brs, 1H, exchangeable with D₂O, NH), 7.50 (s, 1H), 7.41 (m, 3H), 6.73 (s, 2H), 5.09 (s, 2H), 2.18 (s, 2H), 2.10 (s, 6H), 1.05 (s, 9H). MS: 360 (M+1).

N-[4-(3-Fluoro-benzyloxy)-2,6-dimethyl-phenyl]-3,3-dimethyl-butyramide

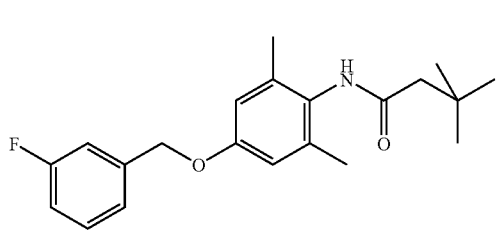

¹H NMR (DMSO-d₆, 400 MHz): δ 8.94 (brs, 1H, exchangeable with D₂O, NH), 7.50 (s, 1H), 7.41 (m, 3H), 6.73 (s, 2H), 5.09 (s, 2H), 2.18 (s, 2H), 2.10 (s, 6H), 1.05 (s, 9H). MS: 360 (M+1).

N-[4-(2,4-Difluoro-benzyloxy)-2,6-dimethyl-phenyl]-3,3-dimethyl-butyramide

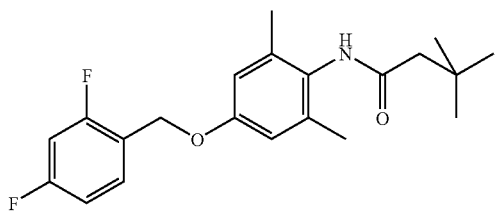

¹H NMR (DMSO-d₆, 400 MHz): δ 8.96 (brs, 1H, exchangeable with D₂O, NH), 7.61 (dd, J=8.3 and 15.3 Hz, 1H), 7.30 (dt, J=2.2 and 10.1 Hz, 1H), 7.13 (dt, J=2.2 and 8.3 Hz, 1H), 6.74 (s, 2H), 5.06 (s, 2H), 2.19 (s, 2H), 2.11 (s, 6H), 1.05 (s, 9H). MS: 362 (M+1).

N-[4-(3,4-Difluoro-benzyloxy)-2,6-dimethyl-phenyl]-3,3-dimethyl-butyramide

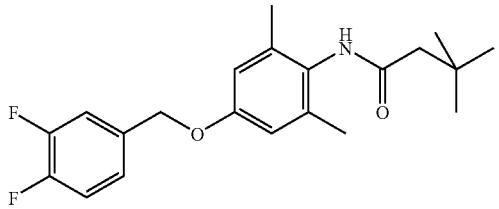

¹H NMR (DMSO-d₆, 400 MHz): δ 8.93 (brs, 1H, exchangeable with D₂O, NH), 7.49 (t, J=7.7 Hz, 1H), 7.43 (dd, J=6.9 and 15.2 Hz, 1H), 7.28 (m, 1H), 6.70 (s, 2H), 5.03 (s, 2H), 2.16 (s, 2H), 2.08 (s, 6H), 1.03 (s, 9H). MS: 362 (M+1).

3-Cyclopentyl-N-[4-(3,4-difluoro-benzyloxy)-2,6-dimethyl-phenyl]-propionamide

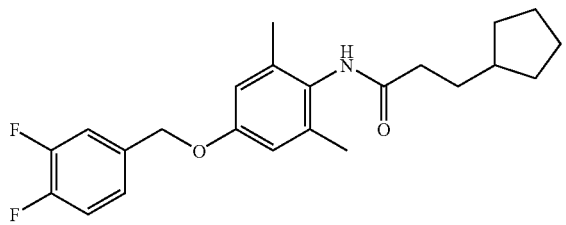

¹H NMR (DMSO-d₆, 400 MHz): δ 8.99 (brs, 1H, exchangeable with D₂O, NH), 7.48 (t, J=7.7 Hz, 1H), 7.42 (dd, J=6.9 and 15.2 Hz, 1H), 7.28 (m, 1H), 6.70 (s, 2H), 5.03 (s, 2H), 2.27 (t, J=6.0 Hz, 2H), 2.06 (s, 6H), 1.75 (m, 3H), 1.60 (m, 4H), 1.47 (m, 2H), 1.10 (m, 2H). MS: 388 (M+1).

3-Cyclopentyl-N-[4-(4-fluoro-benzyloxy)-2,6-dimethyl-phenyl]-propionamide

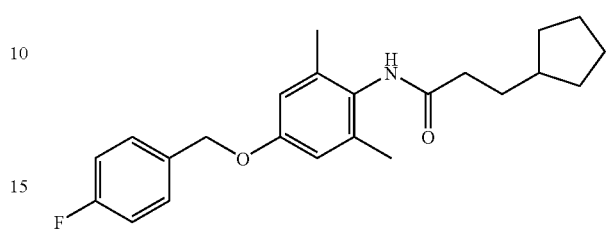

¹H NMR (DMSO-d6, 400 MHz): δ 8.98 (brs, 1H, exchangeable with D2O, NH), 7.46 (dd, J=4.7 and 6.5 Hz, 2H), 7.20 (t, J=7.0 Hz, 1H), 6.69 (s, 2H), 5.02 (s, 2H), 2.28 (t, J=6.0 Hz, 2H), 2.11 (s, 6H), 1.76 (m, 3H), 1.60 (m, 4H), 1.47 (m, 2H), 1.10 (m, 2H). MS: 370 (M+1).

Biological Results

Compounds of this invention formula were evaluated for activity toward potassium channels in a cell-based Rb⁺ efflux assay. This cellular bioassay is believed to faithfully represent the M current channel activities identified with KCNQ2/3 heteromultimers. The most active compounds of this invention have EC₅₀s in the single-digit nM range. Additionally, antiseizure activity in vivo was evaluated in a mouse maximal electroshock seizure (MES) model, and neurotoxicities were determined from a rotorod neurocognitive motor impairment model.

Methods:

Rubidium Efflux Test

PC-12 cells were grown at 37° C. and 5% CO₂ in DMEM/F12 Medium (Dulbecco's Modified Eagle Medium with Nutrient Mix F-12, available from Invitrogen of Carlsbad, Calif.), supplemented with 10% horse serum, 5% fetal bovine serum, 2 mM glutamine, 100 U/ml penicillin, and 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated, and the cells were washed once with 0.2 ml in wash buffer (25 mM HEPES, pH 7.4, 150 mM NaCl, 1 mM MgCl₂, 0.8 mM NaH₂PO₄, 2 mM CaCl₂). The cells were then loaded with 0.2 ml Rb⁺ loading buffer (wash buffer plus 5.4 mM RbCl₂, 5 mM glucose) and incubated at 37° C. for 2 h. Attached cells were quickly washed three times with buffer (same as Rb⁺ loading buffer, but containing 5.4 mM KCl instead of RbCl) to remove extracellular Rb⁺. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for Rb⁺ contents by atomic absorption spectroscopy (see below), they were stored at 4° C. without any negative effects on subsequent Rb⁺ analysis.

The concentrations of Rb⁺ in the supernatants (Rb⁺$_{Sup}$) and the cell lysates (Rb⁺$_{Lys}$) were quantified using an ICR8000 flame atomic absorption spectrometer (Aurora Biomed Inc., Vancouver, B.C.) under conditions defined by the manufacturer. Samples 0.05 ml in volume were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L $Rb^+$ in sample analysis buffer was generated with each set of plates. The percent $Rb^+$ efflux (F) was defined by $$F=[Rb^+_{Sup}/(Rb^+_{Sup}+Rb^+_{Lys})]\times 100\%.$$

wherein the $F_c$ is the efflux in the presence of compound in depolarization buffer, $F_b$ is the efflux in basal buffer, and $F_s$ is the efflux in depolarization buffer, and $F_c$ is the efflux in the presence of compound in depolarization buffer. The efflux (F) and compound concentration relationship was plotted to calculate an $EC_{50}$ value, a compound's concentration for 50% of maximal $Rb^+$ efflux. The results are shown below in Table 1.

Maximal Electroshock Seizure (MES) and Acute Toxicity Tests

MES Test

The MES testing protocol is based on procedures established at the National Institute of Neurological Disorders and Stroke in conjunction with the Anticonvulsant Screening Program (ASP) at the University of Utah (White, H. S., Woodhead, J. H., Wilcox, K. S., Stables, J. P., Kupferberg, H. J and Wolf, H. H. 2002. "General Principles: Discovery and Preclinical Development of Antiepileptic Drugs," in *Antiepileptic Drugs*, 5th Edition, R. H. Levy, ed.; R. H. Mattson, B. S. Meldrum, and E. Perucca. Philadelphia, Lippincott Williams & Wilkins.), The goal of the test rapid identification and characterization of the in vivo anticonvulsant activity of any compounds that have been shown active in PC-12 cellular based $Rb^+$ efflux assay.

Adult male CF-1 albino mice (18-25 g, Charles River Laboratories) are exclusively used for in-house MES screen of compounds. Male Sprague-Dawley albino rats (100-125 g, Charles River Laboratories) are also used to test anticonvulsant compounds. Variability of test outcomes is reduced by using animals of the same sex, age, and weight. Animals are permitted to rest and recover from transit for at least 48 hr prior to experimentation. Animals are used for AED testing only once. In some instances, the animals may be anesthetized prior to blood collection and/or whole brain extraction for pharmacokinetic assay. All animals are maintained and handled as outlined in standard animal care guidelines.

In the experiments, testing compounds are prepared as suspensions in 0.5% methyl cellulose (Sigma, Cat #M0512, Viscosity 4000 cP at 20° C.) in water, regardless of solubility. Dry powder compounds are initially ground with a glass rod in a test tube in several drops of methyl cellulose to create a paste and to break down any large chunks. After several minutes of grinding, the volume of the suspension is increased to the final concentration desired. The suspension is then sonicated using a Branson sonicator model 3510 in a water bath at room temperature for 15 minutes. Compound suspensions are further vortexed prior to animal dosing. In some of the cases, DMSO is used to initially solubilize compounds in small volumes and then this solution is added to the 0.5% methyl cellulose solution, in order to create more even and less aggregated compound suspensions. The final concentration of DMSO is 3.75%, an amount with no apparent toxicity or neuroprotective effects in our usual rotarod and MES tests. Methyl cellulose/DMSO compound suspensions are identically prepared for intraperitoneally (i.p.) to mice or orally (p.o.) to rat dosing.

Initially the animals are weighed with an electronic scale and then marked. Data recording sheets are generated for each compound assessment. Mice or rats are dosed with the compound suspension at 0.01 mL/g of body weight. The typical injection volume range is between 180-250 μl for mice. Compounds are dosed by i.p. to mice using a 25 or 22 gauge needle, depending on the viscosity of the suspension. Rats are p.o. dosed using a flexible feeding tube, typically starting at a compound dose of 5 mg/kg.

A Rodent Electroconvulsive Stimulator (Model 200, Hamit-Darvin-Freesh, Snow Canyon Clinic, Ivins, Utah) is used for MES testing. A 60-Hz alternating current (50 mA for mice; 150 mA for rats) is delivered for 0.2 seconds through corneal electrodes to the mice. A drop of 0.5% tetracaine (Sigma, Cat. #T-7508) solution is placed on the eye prior to current delivery. The electrodes are subsequently placed gently onto the eyes of the animal and the electrical shock is initiated by triggering through a foot-pedal activator. The animals are restrained by hand and gently released as the shock is delivered and the seizure commences. Animals are monitored for hind limb tonic extension as the end point for this test. Current delivery is recorded as a measure of overall seizure-induction potential. Electrical current delivery can vary from approximately 30-55 mA (mice) or 90-160 mA (rats) depending on impedance in the animal and quality of the current delivery (i.e., correct placement of the electrodes on the cornea). Seizures will be successfully induced in control animals throughout this current range. Tonic extension is considered abolished if the hind limbs fail to become fully extended at 180° with the plane of the body. Lack of tonic extension suggests that the test compound has prevented the spread of seizure discharge through neural tissue. Although unnecessary in mice, the rats are pre-screened for seizure induction potential using the MES 24 hr prior to compound dosing and the subsequent MES test. A success rate of 92-100% has been determined for the rat seizure induction potential. Rats that fail to develop tonic/clonic seizures during the pre-screening are not used for drug testing.

For compound testing, time-to-peak effect studies are initially performed using 0.5, 1, 2, 4, 8 and 24 hr time points, typically using a single 5 or 25 mg/kg dose. The determined time-to-peak effect is used for further titration of a compound's potency ($ED_{50}$, the dose of a drug that protects 50% of animals from electrical induced seizure) in both mouse and rat models. For titrations, 8 animals are used per concentration and dose (normal 5 concentrations) is varied until a full dose response curve can be obtained. Probit analysis (ASP method) or non-linear regression analysis on GraphPad (constraining the lower dose/effect value) is used to calculate an $ED_{50}$ value for the test compound.

Rotarod Test

Prior to MES testing, compound dosed mice are scrutinized for abnormal neurologic status as defined by motor impairment on a slowly turning (6 rpm) rotarod apparatus (Model 755, Series 8, IITC Life Sciences, Woodland Hills, Calif.). The inability of a mouse to maintain its balance on the rotarod over a period of one minute (three falls=failure) signifies motor impairment and hence acute toxicity. These measurements are done at the same time points as the MES assay. Untreated normal mice are able to maintain balance on the rotarod for at least one minute without falling. Median toxicity of a compound ($TD_{50}$, the dose of a drug that results in motor impairment in 50% of animals) is determined.

Open Field Test

Before the MES test, compound treated rats are visually observed for acute toxicity signs for approximately one minute in the open field test. Here, rats are gently placed into a plexiglass enclosure and are monitored for behavior consistent with toxicity including ataxia, trembling, hypoactivity (including failure to seek the walls), hypersensitivity, lack of exploratory behavior and lack of avoidance of the open area. Typically if the rats exhibits two or more of these abnormal behaviors they are scored as toxic.

TABLE 1

ACTIVITIES OF EXEMPLARY COMPOUNDS

| COMPOUND | ACTIVITY $EC_{50}$ |
|---|---|
| (4-fluorobenzyl)oxy-phenyl ethyl carbamate | D |
| (4-fluorobenzyl)oxy-fluorophenyl ethyl carbamate | D |
| (4-fluorobenzyl)oxy-methylphenyl ethyl carbamate | D |
| (4-fluorobenzyl)oxy-trifluoromethylphenyl ethyl carbamate | D |
| (3,4-difluorobenzyl)oxy-dimethylphenyl 3-cyclopentylpropanamide | B |
| (3,4-difluorobenzyl)oxy-dimethylphenyl 3,3-dimethylbutanamide | C |

TABLE 1-continued

ACTIVITIES OF EXEMPLARY COMPOUNDS

| COMPOUND | ACTIVITY EC$_{50}$ |
|---|---|
| 4-F-C$_6$H$_4$-CH$_2$-O-(2,6-diMe-C$_6$H$_2$)-NH-C(O)-CH$_2$CH$_2$-cyclopentyl | B |
| 4-F-C$_6$H$_4$-CH$_2$-O-(2,6-diMe-C$_6$H$_2$)-NH-C(O)-CH$_2$-C(CH$_3$)$_3$ | C |
| 4-Me-C$_6$H$_4$-CH$_2$-O-(2,6-diMe-C$_6$H$_2$)-NH-C(O)-CH$_2$-C(CH$_3$)$_3$ | C |
| 3-CF$_3$-C$_6$H$_4$-CH$_2$-O-(2,6-diMe-C$_6$H$_2$)-NH-C(O)-CH$_2$-C(CH$_3$)$_3$ | C |
| 2-CF$_3$-C$_6$H$_4$-CH$_2$-O-(2,6-diMe-C$_6$H$_2$)-NH-C(O)-CH$_2$-C(CH$_3$)$_3$ | D |
| 4-Cl-C$_6$H$_4$-CH$_2$-O-(2,6-diMe-C$_6$H$_2$)-NH-C(O)-CH$_2$-C(CH$_3$)$_3$ | C |

TABLE 1-continued

ACTIVITIES OF EXEMPLARY COMPOUNDS

| COMPOUND | ACTIVITY $EC_{50}$ |
|---|---|
| 4-bromobenzyloxy-2,6-dimethyl-N-(3,3-dimethylbutanoyl)aniline | C |
| 4-trifluoromethylbenzyloxy-2,6-dimethyl-N-(3,3-dimethylbutanoyl)aniline | C |
| 2,4-difluorobenzyloxy-2,6-dimethyl-N-(3,3-dimethylbutanoyl)aniline | C |
| 3-chlorobenzyloxy-2,6-dimethyl-N-(3,3-dimethylbutanoyl)aniline | C |
| 3-fluorobenzyloxy-2,6-dimethyl-N-(3,3-dimethylbutanoyl)aniline | C |

Legend:
A: $EC_{50} \leq 1$ nM;
B: $1$ nM $< EC_{50} \leq 10$ nM;
C: $10$ nM $< EC_{50} \leq 50$ nM;
D: $50$ nM $< EC_{50} \leq 500$ nM Studies of KCNQ2/3 Opening Activity and KCNQ Subtype Selectivity Using Electrophysiological Patch Clamp in *Xenopus* Oocytes Expression in *Xenopus laevis* Oocytes Female *Xenopus laevis* extracted ovaries can be purchased from eNASCO (LM00935MX, eNASCO Fort Atkinson, Wis.). Following manual dissection of the oocytes into smaller groups, the oocytes are defolliculated by enzymatic treatment with collagenase type 2 (LS004177, Worthington, Lakewood, N.J.) for 1½ hour in the presence of calcium-free Culture Bath solution (88 mM NaCl, 1 mM KCl, 0.82 mM MgSO$_4$, 2.4 mM NaHCO$_3$, and 5 mM HEPES, pH 7.5). Oocytes are then kept in supplemented Culture Bath solution (88 mM NaCl, 1 mM KCl, 0.82 mM MgSO$_4$, 0.9 mM CaCl$_2$, 2.4 mM NaHCO$_3$, 1 mM sodium pyruvate, 0.05 mg/ml Geneticin, 100 U/ml penicillin, 0.1 mg/ml streptomycin and 5 mM HEPES, pH 7.5) at 19° C. for 24 hours before injection of cRNA. Approximately 50 nl cRNA (about 50 ng) is injected for KCNQ1, KCNQ4, and KCNQ5 using a Nanoject microinjector (Drummond, Broomall, Pa., USA). For co-expression of KCNQ2 and KCNQ3 and of KCNQ1 and KCNE1, cRNA's are mixed in equal molar ratios before injection of approximately 50 nl. The mixtures contain about 10+10 ng and 12.5+2.5 ng cRNA, respectively. The smaller amounts are needed because larger currents arise when KCNQ2/KCNQ3 and KCNQ1/KCNE1 are co-expressed. Oocytes are kept in Culture Barth solution at 19° C. which is changed daily and currents are recorded after 3 to 5 days.

Electrophysiology

KCNQ channel currents expressed in *Xenopus laevis* oocytes are recorded using a two-electrode voltage-clamp. The recordings are made at room temperature in recording solution (96 mM NaCl, 2 mM KCl, 1 mM $MgCl_2$, 1.8 mM $CaCl_2$, and 5 mM HEPES, pH 7.5) using a two-electrode voltage-clamp amplifier (OC-725C, Warner Instrument, Hamden, Conn., USA). The oocytes are placed in custom built perfusion chambers connected to a continuous flow system and impaled with a current electrode and a voltage-clamp electrode pulled from borosilicate glass on a Flaming/Brown Micropipette Puller (Sutter Instruments Co., Novato, Calif., USA). Recording electrodes are filled with 3 M KCl and had a resistance of 0.5 to 2.5 MΩ.

Compounds

All compounds are dissolved in DMSO to obtain concentrated stock solutions. On the day of electrophysiological experiments the stock solutions are thawed and diluted in recording solution to their final concentrations. The final DMSO concentration never exceeds 0.1%. Compound delivery is performed using a custom built multi-barrel apparatus connected to the flow system.

Calculations

Data are acquired by means of an Axograph X software (Axograph Scientific, Sydney, AU) and analyzed using Graph Pad Prism (GraphPad Software Inc., California, USA).

Concentration—response curves are constructed by plotting the increase in steady-state current expressed in percentages as a function of drug concentration. During the course of the experiment, while various concentrations of the drug are being dosed, the resting voltage is held at −90 mV and pulsed to −60 mV, −40 mV, and −50 mV for 5 s for KCNQ2/KCNQ3, KCNQ4 and KCNQ5 channels respectively. The plot was then fitted to a Hill function:

Response=R2+(R1−R2)/[1+(C/EC$_{50}$)^nH]

wherein R1 is the initial response, R2 is the maximum response, C is the drug concentration and nH is the slope (Hill coefficient) of the curve.

The efficacy of compounds of this invention in comparison with Retigabine (as a positive control) are determined by recording the steady current using the above voltage protocol for the channels in the presence of the EC$_{75}$ of the drugs. After steady channel current is recorded in the presence of Retigabine at its EC75, recorded oocyte is washed with the recording solution until its steady current returned to its normal level without the presence of any drugs. Then the channel steady current is recorded in the presence of the test compound at its EC$_{75}$. The percent efficacy is then expressed as:

% efficacy=(C2/C1)×100% wherein C2 is the recorded steady current in the presence of follow-on compound at its EC$_{75}$ and C1 is the recorded steady current in the presence of Retigabine at its EC$_{75}$.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A compound selected from the group consisting of:

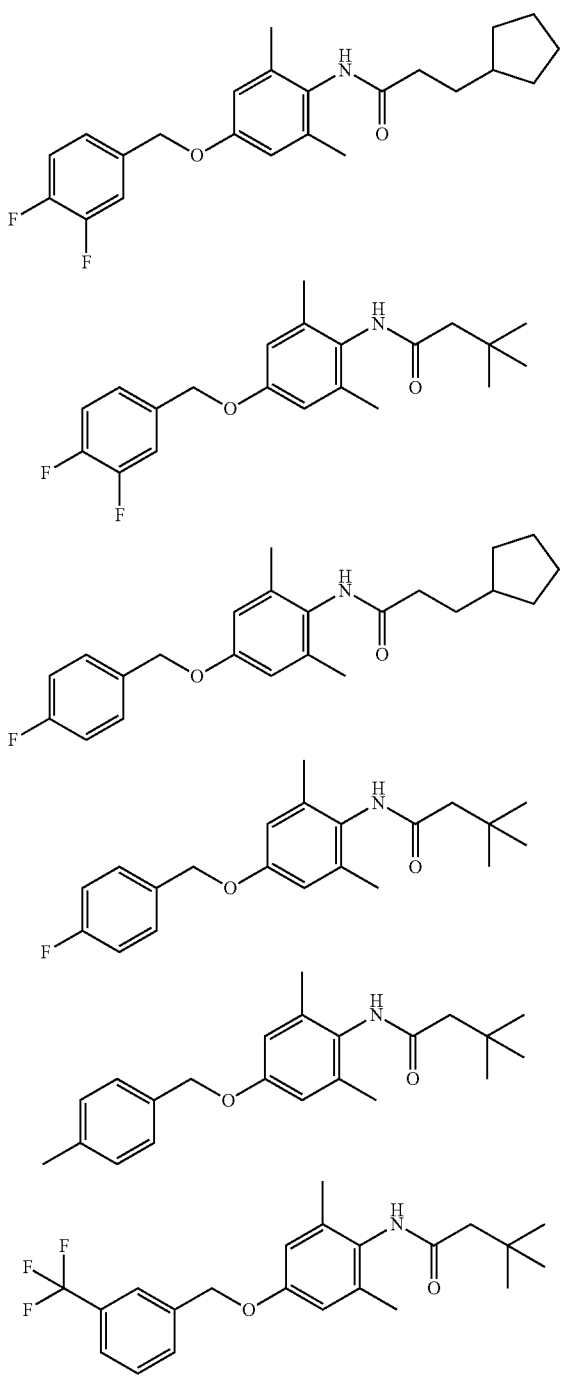

-continued

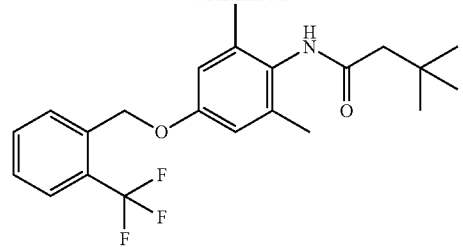

and

-continued

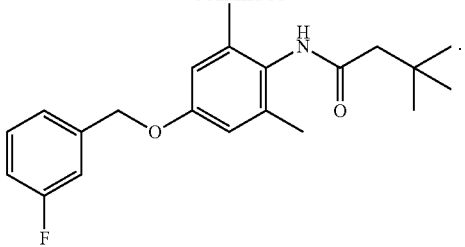

2. A compound selected from the group consisting of:

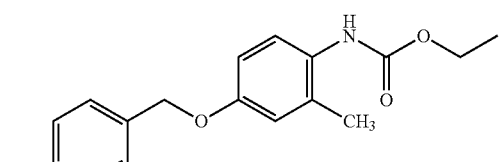

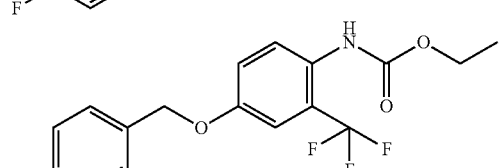

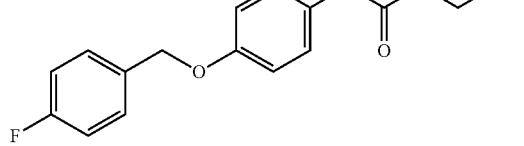

and

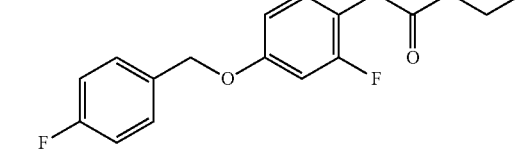

3. A composition comprising a pharmaceutically acceptable carrier and a compound according to claim 1 or a pharmaceutically acceptable salt or ester thereof.

4. A composition comprising a pharmaceutically acceptable carrier and a compound according to claim 2 or a pharmaceutically acceptable salt or ester thereof.

* * * * *